US007828711B2

(12) United States Patent
Ross et al.

(10) Patent No.: US 7,828,711 B2
(45) Date of Patent: *Nov. 9, 2010

(54) METHOD AND APPARATUS FOR MODULATING CELLULAR GROWTH AND REGENERATION USING VENTRICULAR ASSIST DEVICE

(75) Inventors: Jeffrey Ross, Roseville, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1019 days.

This patent is subject to a terminal disclaimer.

(21) Appl. No.: 10/919,016

(22) Filed: Aug. 16, 2004

(65) Prior Publication Data

US 2006/0036126 A1    Feb. 16, 2006

(51) Int. Cl.
A61N 1/362 (2006.01)
A61K 9/22 (2006.01)
A61M 31/00 (2006.01)

(52) U.S. Cl. .................. 600/17; 604/891.1; 604/66
(58) Field of Classification Search ... 604/890.1–890.2, 604/891.1, 892.1, 6.11, 65–67; 607/3, 120, 607/129; 623/1.42; 600/16–18
See application file for complete search history.

(56) References Cited

U.S. PATENT DOCUMENTS

| 4,665,896 | A | * | 5/1987 | LaForge et al. ............ 600/17 |
| 4,686,987 | A | | 8/1987 | Salo et al. |
| 4,756,302 | A | | 7/1988 | Portner et al. |
| 4,930,075 | A | | 5/1990 | Kortas |
| 5,025,786 | A | | 6/1991 | Siegel |
| 5,042,497 | A | | 8/1991 | Shapland |
| 5,103,821 | A | | 4/1992 | King |
| 5,113,869 | A | | 5/1992 | Nappholz et al. |
| 5,130,141 | A | | 7/1992 | Law et al. |
| 5,135,004 | A | | 8/1992 | Adams et al. |
| 5,139,517 | A | | 8/1992 | Corral |

(Continued)

FOREIGN PATENT DOCUMENTS

EP    1050265    11/2000

(Continued)

OTHER PUBLICATIONS

Akiyama-Uchida, Y., et al., "Norepinephrine enhances fibrosis mediated by TGF-beta in cardiac fibroblasts", *Hypertension*, 40(2), (Aug. 2002), 148-54.

(Continued)

*Primary Examiner*—Mark W Bockelman
(74) *Attorney, Agent, or Firm*—Schwegman, Lundberg & Woessner, P.A.

(57) ABSTRACT

A system delivers combined ventricular assist device (VAD) therapy and chemical and/or biological therapy to modulate myocardial tissue growth in a heart after myocardial infarction (MI). The system includes an agent delivery device to release one or more agents to an MI region to modulate myocardial tissue growth in that region, and a VAD to enhance the effects of the one or more agents by reducing myocardial wall stress and the overall cardiac workload. In one embodiment, the system is an implantable system including an implantable agent delivery device and an implantable VAD for long-term use in a patient.

29 Claims, 5 Drawing Sheets

U.S. PATENT DOCUMENTS

| | | |
|---|---|---|
| 5,199,428 A | 4/1993 | Obel et al. |
| 5,251,621 A | 10/1993 | Collins |
| 5,284,136 A | 2/1994 | Hauck et al. |
| 5,352,180 A * | 10/1994 | Candelon et al. .............. 600/17 |
| 5,353,800 A | 10/1994 | Pohndorf et al. |
| 5,404,877 A | 4/1995 | Nolan et al. |
| 5,435,999 A | 7/1995 | Austin |
| 5,486,359 A | 1/1996 | Caplan et al. |
| 5,499,971 A | 3/1996 | Shapland et al. |
| 5,538,722 A | 7/1996 | Blau et al. |
| 5,543,318 A | 8/1996 | Smith et al. |
| 5,558,640 A * | 9/1996 | Pfeiler et al. .................. 604/67 |
| 5,580,779 A | 12/1996 | Smith et al. |
| 5,603,331 A | 2/1997 | Heemels et al. |
| 5,610,172 A | 3/1997 | Weidmann et al. |
| 5,634,899 A | 6/1997 | Shapland et al. |
| 5,662,689 A | 9/1997 | Elsberry et al. |
| 5,681,735 A | 10/1997 | Emerson et al. |
| 5,733,727 A | 3/1998 | Field |
| 5,800,498 A | 9/1998 | Obino et al. |
| 5,817,131 A | 10/1998 | Elsberry et al. |
| 5,833,603 A | 11/1998 | Kovacs et al. |
| 5,833,978 A | 11/1998 | Tremblay |
| 5,865,787 A | 2/1999 | Shapland et al. |
| 5,885,797 A | 3/1999 | Chen et al. |
| 5,914,242 A | 6/1999 | Honkanen et al. |
| 5,928,943 A | 7/1999 | Franz et al. |
| 5,945,577 A | 8/1999 | Stice et al. |
| 5,949,659 A | 9/1999 | Lesche |
| 5,967,986 A | 10/1999 | Cimochowski et al. |
| 5,980,571 A * | 11/1999 | Nomura et al. ............ 623/3.28 |
| 5,991,668 A | 11/1999 | Leinders et al. |
| 5,995,860 A * | 11/1999 | Sun et al. .................... 600/341 |
| 6,005,009 A | 12/1999 | Murad et al. |
| 6,016,447 A | 1/2000 | Juran et al. |
| 6,016,448 A | 1/2000 | Busacker et al. |
| 6,021,350 A | 2/2000 | Mathson |
| 6,066,094 A | 5/2000 | Ben-Haim |
| 6,083,930 A | 7/2000 | Roufa et al. |
| 6,090,622 A | 7/2000 | Gearhart et al. |
| 6,099,832 A | 8/2000 | Mickle et al. |
| 6,100,242 A | 8/2000 | Hammond |
| 6,112,116 A | 8/2000 | Fischell et al. |
| 6,119,554 A | 9/2000 | Plankenhorn |
| 6,135,976 A | 10/2000 | Tachibana et al. |
| 6,140,740 A | 10/2000 | Porat et al. |
| 6,154,675 A | 11/2000 | Juran et al. |
| 6,168,801 B1 | 1/2001 | Heil, Jr. et al. |
| 6,174,871 B1 | 1/2001 | Hammond et al. |
| 6,191,111 B1 * | 2/2001 | Leschinsky .................. 514/12 |
| 6,198,394 B1 | 3/2001 | Jacobsen et al. |
| 6,200,260 B1 | 3/2001 | Bolling |
| 6,200,265 B1 | 3/2001 | Walsh et al. |
| 6,206,914 B1 | 3/2001 | Soykan et al. |
| 6,207,451 B1 | 3/2001 | Dennis et al. |
| 6,213,942 B1 | 4/2001 | Flach et al. |
| 6,224,566 B1 | 5/2001 | Loeb |
| 6,231,516 B1 | 5/2001 | Keilman et al. |
| 6,235,970 B1 | 5/2001 | Stice et al. |
| 6,237,398 B1 | 5/2001 | Porat et al. |
| 6,245,566 B1 | 6/2001 | Gearhart et al. |
| 6,254,573 B1 | 7/2001 | Haim et al. |
| 6,256,233 B1 | 7/2001 | Glass |
| 6,272,377 B1 | 8/2001 | Sweeney et al. |
| 6,277,078 B1 | 8/2001 | Porat et al. |
| 6,284,242 B1 | 9/2001 | Kurachi |
| 6,298,272 B1 | 10/2001 | Peterfeso et al. |
| 6,299,575 B1 | 10/2001 | Bolling |
| 6,306,830 B1 | 10/2001 | Hammond et al. |
| 6,309,370 B1 | 10/2001 | Haim et al. |
| 6,316,419 B1 | 11/2001 | Leiden et al. |
| 6,358,202 B1 | 3/2002 | Arent |
| 6,361,522 B1 | 3/2002 | Scheiner et al. |
| 6,361,780 B1 | 3/2002 | Ley et al. |
| 6,387,037 B1 | 5/2002 | Bolling et al. |
| 6,387,369 B1 | 5/2002 | Pittenger et al. |
| 6,390,969 B1 | 5/2002 | Bolling et al. |
| 6,399,300 B1 | 6/2002 | Field |
| 6,406,422 B1 | 6/2002 | Landesberg |
| 6,410,236 B1 | 6/2002 | Metzger |
| 6,424,847 B1 | 7/2002 | Mastrototaro et al. |
| 6,428,464 B1 | 8/2002 | Bolling |
| 6,436,672 B1 | 8/2002 | Tomlinson |
| 6,436,907 B1 | 8/2002 | Leiden et al. |
| 6,443,949 B2 | 9/2002 | Altman |
| 6,451,594 B1 | 9/2002 | Chien et al. |
| 6,459,917 B1 | 10/2002 | Gowda et al. |
| 6,459,929 B1 | 10/2002 | Hopper et al. |
| 6,468,985 B1 | 10/2002 | Huang |
| 6,501,983 B1 | 12/2002 | Natarajan et al. |
| 6,511,413 B2 | 1/2003 | Landesberg |
| 6,511,477 B2 | 1/2003 | Altman et al. |
| 6,518,245 B1 | 2/2003 | Anderson et al. |
| 6,530,876 B1 | 3/2003 | Spence |
| 6,569,079 B2 | 5/2003 | Arabia et al. |
| 6,596,745 B2 | 7/2003 | Gall |
| 6,604,000 B2 | 8/2003 | Lu |
| 6,610,004 B2 | 8/2003 | Viole et al. |
| 6,610,716 B2 | 8/2003 | Wagle et al. |
| 6,660,737 B2 | 12/2003 | Almstead et al. |
| 6,666,826 B2 | 12/2003 | Salo et al. |
| 6,689,117 B2 | 2/2004 | Sweeney et al. |
| 6,945,998 B2 * | 9/2005 | Liotta .......................... 623/3.2 |
| 6,984,201 B2 * | 1/2006 | Khaghani et al. ............. 600/17 |
| 7,029,466 B2 * | 4/2006 | Altman ....................... 604/508 |
| 7,031,775 B2 * | 4/2006 | Soykan et al. .................. 607/50 |
| 2001/0000802 A1 | 5/2001 | Soykan et al. |
| 2001/0016193 A1 | 8/2001 | Engler |
| 2001/0051148 A1 | 12/2001 | Tremblay |
| 2001/0055590 A1 | 12/2001 | Kurachi |
| 2002/0001577 A1 | 1/2002 | Haverich et al. |
| 2002/0012657 A1 | 1/2002 | Tremblay |
| 2002/0022022 A1 | 2/2002 | Shi et al. |
| 2002/0022259 A1 | 2/2002 | Lee et al. |
| 2002/0031501 A1 | 3/2002 | Law |
| 2002/0031827 A1 | 3/2002 | Kanno et al. |
| 2002/0048800 A1 | 4/2002 | Gu et al. |
| 2002/0055530 A1 | 5/2002 | Neuberger et al. |
| 2002/0077311 A1 | 6/2002 | Leiden et al. |
| 2002/0098167 A1 | 7/2002 | Anversa et al. |
| 2002/0107553 A1 | 8/2002 | Hill et al. |
| 2002/0110910 A1 | 8/2002 | Gwathmey et al. |
| 2002/0124855 A1 | 9/2002 | Chachques |
| 2002/0127210 A1 | 9/2002 | Mickle et al. |
| 2002/0133198 A1 | 9/2002 | Kramer et al. |
| 2002/0142457 A1 | 10/2002 | Umezawa et al. |
| 2002/0147172 A1 | 10/2002 | Podsakoff et al. |
| 2002/0147329 A1 | 10/2002 | Luyten et al. |
| 2002/0161410 A1 | 10/2002 | Kramer et al. |
| 2003/0004403 A1 | 1/2003 | Drinan et al. |
| 2003/0036773 A1 | 2/2003 | Whitehurst et al. |
| 2003/0060854 A1 | 3/2003 | Zhu |
| 2003/0105493 A1 | 6/2003 | Salo |
| 2003/0153952 A1 | 8/2003 | Auricchio et al. |
| 2003/0167081 A1 | 9/2003 | Zhu et al. |
| 2003/0216476 A1 | 11/2003 | Kleemann |
| 2004/0002739 A1 | 1/2004 | Cates et al. |
| 2004/0106954 A1 * | 6/2004 | Whitehurst et al. ............. 607/3 |
| 2004/0158289 A1 | 8/2004 | Girouard et al. |
| 2004/0158290 A1 | 8/2004 | Girouard et al. |
| 2004/0186546 A1 | 9/2004 | Mandrusov et al. |
| 2005/0043675 A1 | 2/2005 | Pastore et al. |
| 2005/0137631 A1 | 6/2005 | Yu et al. |
| 2005/0192637 A1 | 9/2005 | Girouard et al. |

| | | | |
|---|---|---|---|
| 2005/0245972 A1 | 11/2005 | Onyekaba et al. | |
| 2005/0288721 A1* | 12/2005 | Girouard et al. | 607/9 |

FOREIGN PATENT DOCUMENTS

| | | |
|---|---|---|
| EP | 1142607 A2 | 10/2001 |
| WO | WO-9640195 | 12/1996 |
| WO | WO-97/33513 | 9/1997 |
| WO | WO-0017326 | 3/2000 |
| WO | WO-0204063 A1 | 1/2002 |
| WO | WO-0205866 A2 | 1/2002 |
| WO | WO-0249669 A2 | 6/2002 |
| WO | WO-02070065 A2 | 9/2002 |
| WO | WO-2005120635 A1 | 12/2005 |

OTHER PUBLICATIONS

Arnaud, Claire, et al., "iNOS is a mediator of the heat stress-induced preconditioning against myocardial infarction in vivo in the rat", *Cardiovascular Research*, 58, (2003),118-125.

Askari, Arman T., et al., "Targeted Gene Therapy for the Treatment of Cardiac Dysfunction", *Seminars in Thoracic and Cardiovascular Surgery*, 14(2), (Apr. 2002), 167-177.

Aukrust, Pal, et al., "Immunomodulating Therapy: New Treatment Modality in Congestive Heat Failure", *Congest Heart Fail.*, 9(2), (Mar.-Apr. 2003),64-69.

Barbone, Alessandro, et al., "Comparison of right and left ventricular responses to left ventricular assist device support in patients with severe heart failure: a primary role of mechanical unloading underlying reverse remodeling", *Circulation*, 104(6), (Aug. 7, 2001),670-675.

Bigatel, D. A., et al., "The matrix metalloproteinase inhibitor BB-94 limits expansion of experimental abdominal aortic aneurysms", *J Vasc Surg*, 29(1), (1999),130-8.

Boheler, Kenneth R., et al., "Differentiation of Pluripotent Embryonic Stem Cells into Cardiomycocytes", *Circulation Research*, 91(3), (Aug. 9, 2002),189-201.

Bralet, J, et al., "Vasopeptidase inhibitors: an emerging class of cardiovascular drugs", *Trends Pharmacol Sci.*, 22(3), (Mar. 2001),106-9.

Brunner, Friedrich, "Attenuation of myocardial ischemia/reperfusion injury in mice with myocyte-specific overexpression of endothelial nitric oxide synthase", *Cardiovascular Research*,57, (2003),55-62.

Capecchi, M. R., "High efficiency transformation by direct microinjection of DNA into cultured mamalian cells.", *Cells*, 22(2 Pt 2), (Nov. 1980),479-88.

Chu G., "SV40 DNA transfection of cells in suspension: analysis of efficiency of transcription and translation of T-antigen.", *Gene*, 13(2), (Mar. 1981),197-202.

Colonna, P , "Myocardial infarction and left ventricular remodeling: results of the CEDIM trial. Carnitine Ecocardiografia Digitalizzata Infarto Miocardico.", *Am Heart J.*, (Feb. 2000, 139(2 Pt 3)),S124-30.

Colucci, Wilson, S., "Molecular and Cellular Mechanisms of Myocardial Failure", *Am J Cardiol 80(11A)*, (1997),15L-25L.

Condorelli, G , et al., "Cardiomycytes Induce Endothelial Cells to Trans-Differentiate into Cardiac Muscle: Implications for Myocardium Regeneration", *PNAS*, 98(19), (Sep. 11, 2001),10733-10738.

Cserjesi, P. , "Myogein induces the myocyte-specific enhancer binding factor MEF-2 independently of other muscle-specific gene products", *Mol Cell Biol,*(Oct. 1991),4854-62.

Curiel, D. T., et al., "Adenovirus enhancement of transferrin-polysine-mediated gene delivery", *Proc Natl Acad Sci USA.*, 88(19), (Oct. 1, 1991),8850-4.

Depre, Christophe , et al., "Metabolic Aspects of Programmed Cell Survival and Cell Death in The Heart", *Cardiovascular Research*, 45(3), (Feb. 2000),538-548.

Dhawan, J. , "Tetracycline-regulated gene expression following direct gene transfer into mouse skeletal muscle", *Somat Cell Mol Genet.*, 21(4), (1995),233-40.

Eckardt, Lars , et al., "Load-induced in repolarization: evidence from experimental and clinical data", *Basic Res Cardiol*, 96(4), (2001),369-380.

Felgner, P. L., "Lipofection: A highly efficient, lipid-mediated DNA-transfection procedure", *Proceedings of the National Academy of Sciences*, 84, Biochemistry,(Nov. 1987),pp. 7413-7417.

Ferdinandy, Peter , et al., "Nitric oxide, superoxide, and peroxynitrie in myocardial ischaemia-reperfusion injury and preconditioning", *British Journal of Pharmacology*, 138(4), (2003),532-543.

Flogel, Ulrich , "Myoglobin: A scavenger of bioactive NO", *PNAS*, 98(2), (Jan. 16, 2001),735-740.

Freedman, Saul B., et al., "Therapeutic Angiogenesis for Ischemic Cardiovascular Disease", *J. Mol Cell Cardiol.*, 33(3), (Mar. 2001),379-393.

Gewaltig, Michael T., "Vasoprotection by nitric oxide: mechanisms and therapeutic potential", *Cardiovascular Research*, 55, (Feb. 14, 2002),250-260.

Graham, F. L., "A New Technique for the Assay of Infectivity of Human Adenovirus 5 DNA", *Virology*, 52, (1973),456-467.

Graham, Regina M., et al., "Gene and Cell Therapy for Heart Disease", *IUBMB Life*, 54, (2002),59-66.

Hafizi, S. , et al., "Inhibition of human cardiac fibroblast mitogenesis by blockade of mitogen-activated protein kinase and phosphatidylinositol 3-kinase.", *Cir Exp Pharma Physiol*, 26(7), (Jul. 1999),511-3.

Hakuno, Daihiko , et al., "Bone Marrow-Derived Regenerated Cardiomyocytes (CMG Cells) Express Functional Adrenergic and Muscarinic Receptors", *Circulation*, 105, (Jan. 22, 2002),380-386.

Hammond H. K., et al., "Regional myocardial downregulation of the inhibitory guanosine triphosphate-binding protein (Gi alpha 2) and beta-adrenergic receptors in a porcine of chronic myocardial ischemia", *J Clin Res*, 92(6), (1993),2644-52.

Harjai, Kishore J., et al., "Therapeutic Angiogenesis: a Fantastic New Adventure", *Journal of Interverntional Cardiology*, 15(3), (2002),223-229.

Heerdt, Paul M., et al., "Chronic Unloading By Left Ventricular Assist Device Reverses Contractile Dysfunction and Alters Gene Expression in End-Stage Heart Failure", *Circulation*, 102(22), (Nov. 28, 2000),2713-2719.

Higashi, T. , et al., "Pharmacological characterization of endothelin-induced rat pulmonary arterial dilatation", *Br J Pharmacol*, 121(4), (1997),782-6.

Isner, Jeffrey M., "Myocardial Gene Therapy", *Nature 415*, (Jan. 10, 2002),234-239.

Jackson, Kathyjo A., et al., "Regeneration of Ischemic Cardiac Muscle and Vascular Endothelium By Adult Stem Cells", *The Journal of Clinical Investigation*, vol. 107, No. 11,, (Jun. 2001),pp. 1395-1402.

Jain, Mohit , "Cell therapy attenuates deleterious ventricular remodeling and improves cardiac performance after myocardial infarction", *Circulation*, 103(14), (Apr. 10, 2001),1920-1927.

Johnson, J. E., "Muscle creatine kinase sequence elements regulating skeletal and cardiac muscle expression in transgenic mice", *Mol Cell Biol.*, 9(8), (1989),3393-9.

Jugdutt, Bodh, I., "Remodelling of the Myocardium and Potential Targets in the Collagen Degradation and Synthesis Pathways", *Current Drug Targets Cardiovascular & Haematological Disorders*, 3, (2003),1-30.

Kehat, Izhak , et al., "Human Embryonic stem Cells Can Differentiate into Myocytes with Structurual and Functional Properties of Cardiomycytes"*The Journal of Clinicial Investigation*, vol. 108, No. 3,, (Aug. 2001),pp. 363-364.

Kiba, A. , et al., "VEGFR-2-specific ligand VEGF-E induces non-edematous hyper-vascularization in mice.", *Biochem Biophys Res Commun.*, 301(2), (Feb. 7, 2003),371-7.

Klein, T. M., "High-Velocity Microprojectiles for Delivering Nucleic Acids into Living Cells", *Nature*, 327 (1987),70-73.

Kocher, A A., et al., "Neovascularization of Ischemic Myocardium by Human Bone-Marrow-Derived Angioblasts Prevents Cardiomyocyte Apoptosis, Reduces Remodeling and Improves Cardiac Function", *Nature Medicine*, vol. 7, No. 4,, (Apr. 2001),pp. 430-436.

Kodama, I. , et al., "Cellular electropharmacology of amiodarone.", *Cardiovas Res*, 35(1), (1997),13-29.

Komuro, Issei , et al., "Control of Cardiac Gene Expression by Mechanical Stress", *Annu Rev Physiol.,*, (1993),pp. 55-75.

Laham, Roger J., et al., "Gene Transfer to Induce Angiogenesis in Myocardial and Limb Ischaemia", *Expert Opin Biol Ther.*, 1(16),, (2001),pp. 985-994.

Lehman, J , et al., "Gene regulaory mechanisms governing energy metabolism during cardiac hypertrophic growth", *Heart Fail Rev.*, (Apr. 2000),175-85.

Levin, L , "Researchers present findings at European cardiology conference", *Advisory Board Daily Briefing, 8. Clinical Outlook*, (Sep. 2002),8 pages [see pp. 5,6].

Li, Qianghong , "Gene Therapy With Inducible Nitric Oxide Synthase Protects Against Myocardial Infaction via a Cyclooxygenase-2-Dependent Mechanism", *Circulation Research*, 92, (2003),741-748.

Lijnen, P. J., et al., "Induction of Cardiac Fibrosis by Transforming Growth Factor-B1", *Molecular Genetics and Metabolism*, 71, (2000),418-435.

Lodie, Tracey A., et al., "Systematic Analysis of Reportedly Distinct Populations of Multipotent Bone Marrow-Derived Stem Cells Reveals a Lack of Distinction", *Tissue Engineering*, vol. 8. No. 5,, (2002),pp. 739-751.

Lopaschuk, G , "Metabolic abnormalities in the diabetic heart", *Heart Fail Rev.*, 7(2), (Apr. 2002),149-59.

Losordo, Douglas W., et al., "Gene Therapy for Myocardial Angiogenesis", *Am Heart J.*, vol. 138., (1999),pp. S132-S141.

Lovett, Eric G., "Technique for Discriminating Between Coordinated and Uncoordinated Cardiac Rhythms", U.S. Appl. No. 10/435,487, filed May 9, 2003, assigned to Cardiac Pacemakers, Inc.,(May 9, 2003),36 pgs.

Luepker, R. , "Transthoracic Electrical Impedance: Quantitative Evaluation of a Non-Invasive Measure of Thoracic Fluid Volume", *American Heart Journal*, 85(1), (Jan. 1973),83-93.

MacKenna, Deidre , et al., "Role of mechanical factors in modulating cardia fibroblast function and extracellular matrix synthesis", *Cardiovascular Research*, 46, (2000),257-263.

Mader, S. , "A steroid-induced promoter for the controlled overexpression of cloned genes in eukaryotic cells", *Proc Natl Acad Sci USA*, 90(12), (1993),5603-7.

Mai, J. , "Enhanced Rate Response Algorithm for Orthostatic Compensation Pacing", *Pacing Clin Electrophysiol. (PACE) Abstracts*, 23 (Pt 2), (Apr. 2000),722.

Mann, Brenda K., "Tissue Engineering in the Cardiovascular System: Progress Toward a Tissue Engineered Heart", *Anat Rec.* 263., (2001),pp. 367-371.

Mannino, R. J., "Liposome mediated gene transfer.", *BioTechniques*, 6(7), (Jul.-Aug., 1988),682-90.

Menasche, Philippe , "Cell Theraph of Heart Failure", *CR Biologies*, vol. 325., (2002),pp. 731-738.

Min, Mart , et al., "Electrical Impedance and Cardiac Monitoring-Technology, Potential and Applications", *International Journal of Bioelectromagnetism*, 5(1), (2003),53-56.

Miyagawa, Shigeru , et al., "Myocardial Regeneration Therapy for Heart Failure: Hepatocyte Growth Factor Enhances The Effect of Cellular Cardiomyoplasty", *Circulation*, 105(21), (May 28, 2002),2556-2561.

Muscat, G. E., "Multiple 5'-flanking regions of the human alpha-skeletal actin gene synergistically modulate muscle-specific expression", *Mol Cell Biol*, 7(11), (1987),4089-99.

Nemer, Georges , et al., "Regulation of Heart Development and Function Through Combinatorial Interactions of Transcription Factors", *The Finnish Medical Society Duodecim, Ann Med.* vol. 33,, (2001),pp. 604-610.

Orlic, Donald , et al., "Bone Marrow Cells Regenerate Infarcted Myocardium", *Nature*, vol. 410,, (Apr. 5, 2001),pp. 701-705.

Ostadal, Pets , et al., "The effect of early treatment by cerivastatin on the serum level of C-reactive protein, interleukin-6, and interleukin-9 in patients with unstable angina and non-Q-wave myocardial infarction", *Molecular and Cellular Biochemistry*, 246, (2003),45-50.

Palermo, J. , "Transgenic remodeling of the contractile apparatus in the mammalian heart", *Circ Res*, 78(3), (1996),504-9.

Paolocci, Nazareno , et al., "Positive inotropic and lusitropic effects of HNO/NO- in failing hearts: Independence from beta-adrenergic signaling", *Proceedings of the National Academy of Sciences USA*, 100(9), (Apr. 29, 2003),5537-5542.

Pasumarthi, Kishore B., et al., "Cardiomyocyte Cell Cycle Regulation", *Circ Res.*, vol. 90,, (2002),pp. 1044-1054.

Pimentel, Rhea C., et al., "Autocrine Regulation of Myocyte Cx43 Expression by VEGF", *Circ Res.*, 90:, (2002),pp. 671-677.

Pouleur, H. , et al., "Changes in plasma renin activity and haemodynamics during vasodilator therapy in conscious dogs with myocardial infarction or chronic volume overload.", *Eur J Clin Investig*, 13(4), (1983),331-8.

Pouzet, B. , et al., "Intramyocardial transplantation of autologous myoblasts: can tissue processing be optimized?", *Circulation*, 102(19 Suppl 3), (2000),III210-5.

Prinzen, Frits W., et al., "Mapping of Regional Myocardial Strain and Work During Ventricular Pacing: Experimental Study Using Magnetic Resonance Imaging and Tagging", *Journal of American College of Cardiology*, vol. 33, No. 6,, (1999),pp. 1735-1742.

Reinecke, Hans , et al., "Survival, Integration and Differentiation of Cardiomycocyte Grafts: a Study in Normal and Injured Rat Hearts", *Circulation*,, (1999),pp. 193-202.

Rinsch, C. , et al., "Delivery of FGF-2 but not VEGF by encapsulated genetically engineered myoblasts improves survival and vascularization in a model of acute skin flap ischemia", *Gene Therapy*, 8, (2001),523-533.

Rizos, I , "Three-year survival of patients with heart failure caused by dilated cardiomyopathy and L-carnitine administration", *Am Heart J.*, 139(2 Pt 3), (Feb. 2000),Am Heart J.

Robbins, Jeffrey , "Remodeling the Cardiac Sarcomere Using Transgenesis", *Annu Rev Physiol.*, vol. 62., (2000),pp. 261-287.

Roth, D. A., et al., "Downregulation of cardiac guanosine 5'-triphosphate-binding proteins in right atrium and left ventricle in pacing-unduced congestive heart failure", *J Clin Invest.*, 91(3), (Mar. 1983),939-49.

Sabbah, H , et al., "Partial fatty acid oxidation inhibitors: a potentially new class of drugs for heart failure", *Eur J Heart Fail.*, 4(1), (Jan. 2002),3-6.

Salloum, Fadi , "Sildenafil Induces Delayed Preconditioning Through Inducible Nitric Oxide Synthase-Dependent Pathway in Mouse Heart", *Circulation Research*, 92, (Apr. 4, 2003),595-597.

Sam, Flora , et al., "Role of Endothelin-1 in Myocardial Failure", *Proceedings of the Association of American Physicians*, 111(5), (1999),417-422.

Semenza, G. L., "Hypoxia-inducible nuclear factors bind to an enhancer element located 3' to the human erythropoietin gen", *Proc Natl Acad Sci USA*, 88(13), (1991),5680-4.

Semenza, G. L., "Transcriptional regulation of genes encoding glycolytic enzymes by hypoxia-inducible factor 1", *J Biol Chem*, 269(38), (1994),23757-63.

Shigekawa, K. , "Electroporation of Eukaryotes and Prokaryotes: A General Approach to the Induction of Macromolecules into Cells", *BioTechniques*, 6, (1988),742-751.

Shockett, P. , "A modifified tetracycline-regulated system provides autoregulatory, inducible gene expression in cultured cells and transgenic mice", *Proc Natl Acad Sci USA*, 92(14), (1995),6522-6.

Stanley, W , et al., "Energy metabolism in the normal and failing heart: potential for therapeutic interventions", *Heart Fail Rev.*, (Apr. 2002),115-30.

Stanley, W , "Partial fatty acid oxidation inhibitors for stable angina", *Expert Opin Investig Drugs*, 11(5), (May 2002),615-29.

Suematsu, Yoshihiro , et al., "L-Arginine given after ischaemic preconditioning can enhance cardioprotection in isolated rat hearts", *European Journal of Cardio-thoracic Surgery*, 19, (2001),873-879.

Sukenaga, Y. , et al., "Development of the chymase inhibitor as an anti-tissue-remodeling drug: myocardial infarction and some other possibilities", *Jap J Pharmacol*, 90(3), (2002),218-22.

Suzuki, Ken , "Cell Transplantation for the Treatment of Acute Myocardial Infarction Using Vascular Endothelial Growth Factor-Expressing Skeletal Myoblasts", *Circulation*; 104[suppl I], (2001),I-207-I-212.

Taylor, D. A., et al., "Delivery of primary autologous skeletal myoblasts into rabbit heart by coronary infusion: a potential approach to myocardial repair", *Proc Assoc Am Phys*, 109(3), (May 1997),245-53.

Taylor, Doris A., et al., "Regenerating Functional Myocardium: Improved Performance after Skeletal Myoblast Transplantation", *Nature Medicine*, vol. 4, No. 8,, (Aug. 1998),pp. 929-933.

Terracio, Louis , "Effects of Cyclic Mechanical Stimulation of the Cellular Components of the Heart: In Vitro.", *In Vitro Cellular & Developmental Biology*, 24(1), (Jan. 1988),53-58.

Villarreal, F. J., "Human cardiac fibroblasts and receptors for angiotensin II and bradykinin: A potential role for bradykinin in the modulation of cardiac extracellular matrix", *Basic research in cardiology*, 93 Supp 3, (1998),s004-s007.

Walter, Dirk H., "Endothelial progenitor cells: regulation and contribution to adult neovascularization", *Herz*, 27(7), (2002),579-588.

Washizu, Masao , et al., "Handling Biological Cells Using a Fluid Integrated Circuit", *IEEE Transactions on Industry Applications*, vol. 26, No. 2, (Mar./Apr. 1990),352-358.

Weintraub, H. , "The myoD gene family: nodal point during specification of the muscle cell lineage", *Science*, 251(4995), (Feb. 15, 1991),761-6.

Wobus, Anna M., et al., "Embryonic Stem CellDerived Cardiac Differentiation: Modulation of Differentiation and "Loss of_Function" Analysis In Vitro", *TCM*. vol. 8, No. 2,, (1998),pp. 64-74.

Woldbaek Per R., et al., "Increased cardiac IL-18 mRNA, pro-IL-18 and plasma IL-18 after myocardial infarction in the mouse; a potential role in cardiac dysfunction", *Cardiovascular Research*, 59, (2003),122-131.

Wolff, A , et al., "Metabolic approaches to the treatment of ischemic heart disease: the clinicians' persepective", *Heart Fail Rev*., (Apr. 2002),187-203.

Wolfrum, Sebastian , et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharmacol*, vol. 41, No. 3, (Mar. 2003),474-480.

Wunderlich, Carsten , "Acute Inhibition of Myoglobin Impairs Contractility and Energy State of iNOS-Overexpressing Hearts", *Circulation Research*, 92, (2003),1352-1358.

Wynn, R , "Cardiovascular drugs and dental considerations", *Cardiovascular drugs and dental considerations. J Calif Dent Assoc*., 28(7), (Jul. 2000),9-26.

Xu, Chunhui , et al., "Characterization and Enrichments of Cardiomyocytes Derived from Human Embryonic Stem Cells", *Circ Res*., vol. 91,, (2002),pp. 501-508.

Yagi, A. , et al., "Anti-inflammatory constituents, aloesin and aloemannan in Aloe species and effects of tanshinon VI in *Salvia miltiorrhiza* on heart", *J Pharm Soc Japan*, 123(7), (Jul. 2003),514-32.

Zhuang, Jianping , et al., "Pulsatile Stretch Remodels Cell-to-Cell Comunication in Cultured Myocytes", *Circ Res*., 87,, (2000),pp. 316-322.

Zimmermann, W. H., et al., "Tissue engineering of a differentiated cardiac muscle construct", *Circulation Res*., 90(2), (2002),223-30.

"U.S. Appl. No. 10/862,716, Response filed Nov. 19, 2008 to Final Office Action mailed Aug. 20, 2008", 11 pgs.

"U.S. Appl. No. 10/862,716, Notice of Allowance mailed Mar. 23, 2010", 4 pgs.

"U.S. Appl. No. 10/862,716, Notice of Allowance mailed Dec. 1, 2009", 4 Pgs.

"U.S. Appl. No. 10/862,716, Response filed May 20, 2008 to Restriction Requirement mailed Apr. 21, 2008", 10 pgs.

"U.S. Appl. No. 10/862,716, Restriction Requirement mailed Apr. 21, 2008", 5 pgs.

"European Application No. 05757159.8, Communication mailed Mar. 16, 2007", 2 pgs.

"European Application No. 05757159.8, Office Action received Oct. 29, 2009", 3 pgs.

"European Application No. 05757159.8, Response filed Apr. 24, 2007 to Communication mailed Mar. 16, 2007", 16 pgs.

"International Application No. PCT/US2005/01931, International Search Report and Written Opinion mailed Oct. 6, 2005", 15 pgs.

"U.S. Appl. No. 10/862,716, Non-Final Office Action mailed May 1, 2009", 9 pgs.

"U.S. Appl. No. 10/862,716, Response filed Feb. 4, 2009 to Restriction Requirement mailed Dec. 5, 2008", 23 pgs.

"U.S. Appl. No. 10/862,716, Response filed Jun. 30, 2009 to Non Final Office Action mailed May 1, 2009", 10 pgs.

\* cited by examiner

METHOD AND APPARATUS FOR MODULATING CELLULAR GROWTH AND REGENERATION USING VENTRICULAR ASSIST DEVICE

CROSS-REFERENCE TO RELATED APPLICATION

This application is related to co-pending, commonly assigned U.S. patent application Ser. No. 10/862,716, entitled "METHOD AND APPARATUS TO MODULATE CELLULAR REGENERATION POST MYOCARDIAL INFARCT," filed on Jun. 7, 2004, which is hereby incorporated by reference in its entirety.

FIELD OF THE INVENTION

This document generally relates to cardiac rhythm management (CRM) systems and particularly, but not by way of limitation, to such systems including a ventricular assist device (VAD) and an agent delivery device to deliver combined VAD and agent therapies.

BACKGROUND OF THE INVENTION

The heart is the center of a person's circulatory system. It includes an electromechanical system performing two major pumping functions. The heart includes four chambers: right atrium (RA), right ventricle (RV), left atrium (LA), and left ventricle (LV). The left portions of the heart, including LA and LV, draw oxygenated blood from the lungs and pump it to the organs of the body to provide the organs with their metabolic needs for oxygen. The right portions of the heart, including RA and RV, draw deoxygenated blood from the body organs and pump it to the lungs where the blood gets oxygenated. The efficiency of the pumping functions, indicative whether the heart is normal and healthy, is indicated by measures of hemodynamic performance, such as parameters related to intracardiac blood pressures and cardiac output.

In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply. The adult heart lacks a substantial population of precursor, stem cells, or regenerative cells. Therefore, after MI, the heart lacks the ability to effectively regenerate cardiomyocytes to replace the injured cells in the infarcted areas of the myocardium. Each injured area eventually becomes a fibrous scar that is non-conductive and non-contractile. Consequently, the overall contractility of the myocardium is weakened, resulting in decreased cardiac output. As a physiological compensatory mechanism that acts to increase cardiac output in response to MI, the LV diastolic filling pressure increases as the pulmonary and venous blood volume increases. This increases the LV preload (stress on the LV wall before its contracts to eject blood). One consequence is the progressive change of the LV shape and size, a processes referred to as remodeling. Remodeling is initiated in response to a redistribution of cardiac stress and strain caused by the impairment of contractile function in the infarcted tissue as well as in nearby and/or interspersed viable myocardial tissue with lessened contractility due to the infarct. The remodeling starts with expansion of the region of the infarcted tissue and progresses to a chronic, global expansion in the size and change in the shape of the entire LV. Although the process is initiated by the compensatory mechanism that increases cardiac output, the remodeling ultimately leads to further deterioration and dysfunction of the myocardium. Consequently, post MI patients experience impaired hemodynamic performance and have a significantly increased risk of developing heart failure.

What is needed is a method with long term effectiveness in treating myocardial injuries after MI.

SUMMARY OF THE INVENTION

A system delivers combined ventricular assist device (VAD) therapy and agent therapy to modulate myocardial tissue growth in a heart after myocardial infarction (MI). The agent therapy includes delivering one or more chemical, biochemical, and/or biological agents.

In one embodiment, a system includes an agent delivery device and a ventricular-assist device (VAD). The agent delivery device contains one or more agents that modulate myocardial tissue growth and delivers the one or more agents to an MI region in a heart. The VAD includes a pump and a controller. The pump assists the heart in blood pumping. The controller controls the operation of the pump for enhancing one or more effects of the one or more agents in the modulation of myocardial tissue growth.

In one embodiment, a method is provided for promoting tissue growth in a heart having an MI region. One or more agents are delivered to the heart in an amount effective to modulate myocardial tissue growth in the MI region. The heart is provided with assistance in blood pumping using a VAD. The VAD operates to enhance one or more effects of the one or more agents in modulating the myocardial tissue growth.

In one embodiment, a method is provided for modulating scar formation at a site of myocardial injury in an animal. A VAD therapy is delivered. One or more agents are delivered to modulate fibrosis to an animal having a myocardial injury. The VAD therapy is delivered to reduce cardiac wall stress and/or to alter cardiac workload. At least one agent is administered in an amount effective to modulate fibrosis scarring at a site of myocardial injury.

In one embodiment, a method is provided for enhancing replacement of tissue at a site of myocardial injury in an animal. A VAD therapy is delivered. One or more agents are administered to promote stem cell migration, implantation and/or proliferation to an animal having a myocardial injury. The VAD therapy is delivered to cardiac tissue so as to reduce cardiac wall stress and/or to alter cardiac workload. At least one agent is administered in an amount effective to enhance stem cell localization, implantation and/or proliferation at a site of myocardial injury.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document. The drawing are for illustrative purposes only and not to scale nor anatomically accurate.

DETAILED DESCRIPTION OF THE INVENTION

Figure 1:
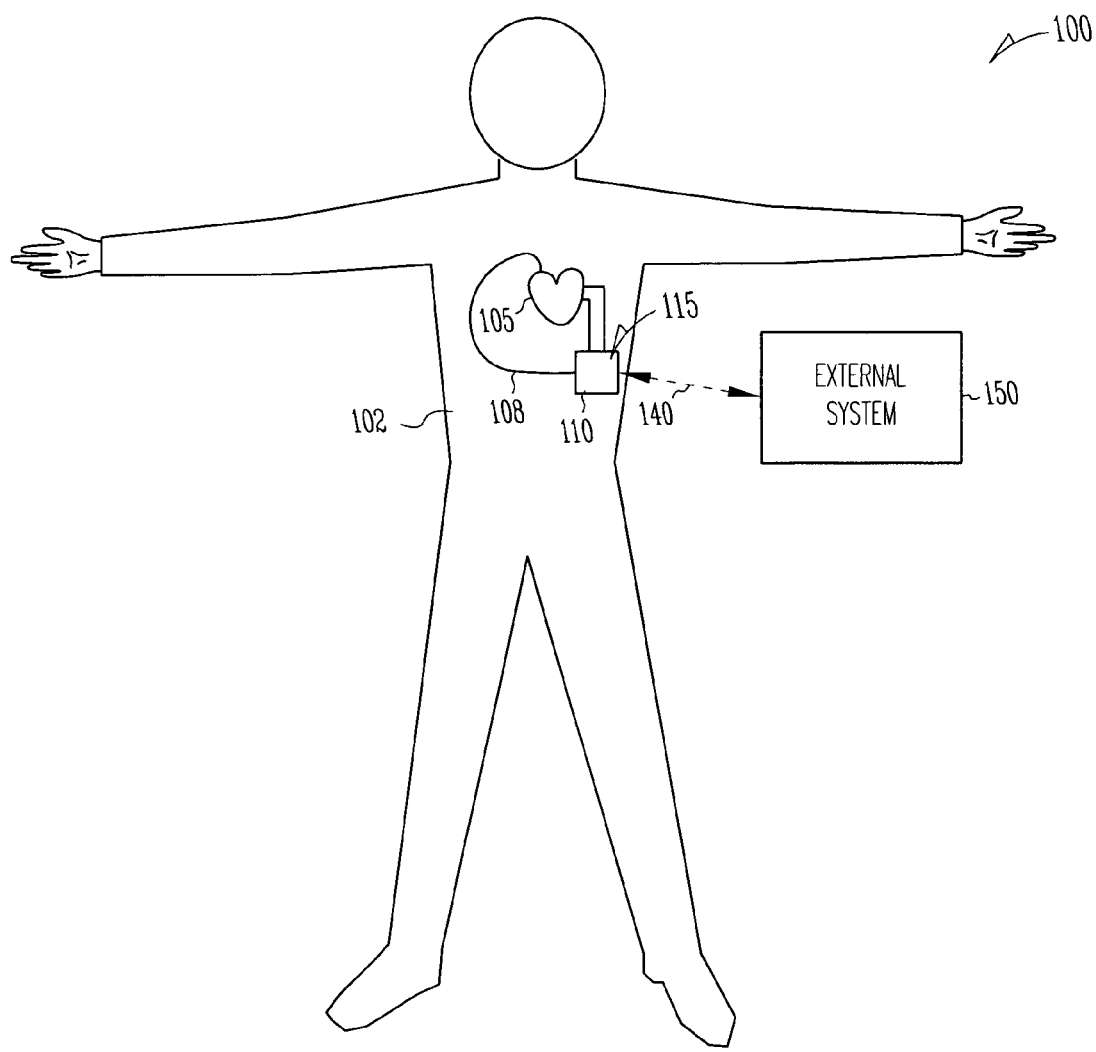
FIG. 1 is an illustration of an embodiment of a system delivering combined VAD and agent therapies to a heart and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

Definitions

A "cytokine" is a relatively low molecular weight protein secreted by cells, e.g., cells of the immune system, for the purpose of altering the function(s) of those cells and/or adjacent cells. Cytokines include interleukins, e.g., molecules which regulate the inflammatory and immune response, as well as growth and colony stimulating factors.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, recombinant viral vectors (such as recombinant adenoviruses, adeno-associated viruses (AAV), lentiviruses, herpes-virus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Large varieties of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA,* 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source, or to cells which have not been genetically modified, i.e., nonrecombinant cells. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector, e.g., a replication-defective viral vector.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer element" is meant a nucleic acid sequence that, when positioned proximate to a promoter, confers increased transcription activity relative to the transcription activity resulting from the promoter in the absence of the enhancer domain. By "cardiac-specific enhancer element" is meant an element, which, when operably linked to a promoter, directs gene expression in a cardiac cell and does not direct gene expression in all tissues or all cell types. Cardiac-specific enhancers of the present invention may be naturally occurring or non-naturally occurring. One skilled in the art will recognize that the synthesis of non-naturally occurring enhancers can be performed using standard oligonucleotide synthesis techniques.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" as used herein includes vertebrates such as avians, amphibians, reptiles, fish and other aquatic organisms.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide or polypeptide or cell refers to a nucleic acid sequence, peptide, polypeptide or cell that is identified and separated from at least one contaminant nucleic acid, polypeptide or other biological component with which it is ordinarily associated in its natural source. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished.

By "growth factor" is meant an agent that, at least, promotes cell growth or induces phenotypic changes.

The term "angiogenic growth factor" means an agent that alone or in combination with other agents induces angiogenesis, and includes, but is not limited to, fibroblast growth factor (FGF), vascular endothelial growth factor (VEGF), hepatocyte growth factor, angiogenin, transforming growth factor (TGF), tissue necrosis factor (TNF, e.g., TNF-α), platelet derived growth factor (PDGF), granulocyte colony stimulatory factor (G-CSF), placental GF, IL-8, proliferin, angiopoietin, e.g., angiopoietin-1 and angiopoietin-2, thrombospondin, ephrin-A1, E-selectin, leptin and heparin affinity regulatory peptide.

The term "agents," as used in this document, include agents that are chemical and/or biological in origin.

As used herein, "vascularization" (formation of vessels that are capable of conducting fluid) includes vasculogenesis and angiogenesis. Vasculogenesis is the organization of undifferentiated endothelial cells into vascular structures. Vasculogenesis may be followed by angiogenesis, whereby previously formed vessels extend into undervascularized regions. During angiogenesis, endothelial cells proliferate and extend from previously formed vessels, forming new vascular structures.

Combined VAD and Agent Therapies

This document describes, among other things, method and apparatus for VAD therapy and agent therapy of myocardial tissue, e.g., tissue which has been injured by MI. In one embodiment, agent therapy is applied to tissue by locally administering to a recipient animal one or more agents, e.g., a drug, protein, glycoprotein, peptide, or a vector, to tissue in vivo. In one embodiment, the area including the damaged tissue is subjected to VAD and chemical therapy while in other embodiments the tissue is subjected to VAD therapy, chemical therapy and biological therapy, e.g., inserting or applying, appropriate cellular material ("donor cells") into and/or to the tissue. In a further embodiment, the area is also subjected to electrical therapy, such as pacing therapy. The donor cells may be ones expanded ex vivo, including those subjected to in vitro conditioning as described below, including those which are genetically modified.

VAD therapy may be applied before, during, or after agent therapy, or any combination thereof. In one embodiment, agent administration is for a period of time during VAD therapy. In another embodiment, agent administration is initiated before VAD therapy and optionally continues for a period during VAD therapy. In another embodiment, an agent is administered, and then VAD therapy is initiated. In one approach, donor cells are administered concurrently with VAD and/or agent therapy, while in other approaches VAD and agent therapies are initiated subsequent to cell administration. In another approach, VAD and agent therapies are applied prior to cell administration. In one approach, cellular engraftment, cellular proliferation, cellular differentiation, cellular survival and/or cellular function, e.g., contractile function, of the donor cells in the recipient is further enhanced by the VAD therapy and/or agent administration. It is understood that different permutations of agent, cell and/or VAD therapy may be performed in varying embodiments.

In an animal model of MI, efficacious VAD and agent therapy may result in improvement in cardiac function, e.g., increased maximum exercise capacity, contractile performance, and propagation velocity, decreased deleterious remodeling, decreased post-scar expansion, decreased apoptosis, increased angiogenesis, and increased cell engraftment, survival, proliferation, and function, or a combination thereof. In ex vivo models, effects in hemodynamic performance, such as indicated by systolic and diastolic pressure-volume relations, can be used to determine the efficacy of a particular therapy.

System for Therapy Delivery

A system provides combined VAD and agent therapies to treat a heart having suffered MI. The VAD and agent therapies combine artificial blood pumping and delivery of one or more agents including biological agents, e.g., those encoded by DNA or isolated from cells, to reduce scar formation and/or promote myocardial tissue growth, e.g., replacement, in the infarct region. The one or more agents modulate myocardial tissue growth, such as by promoting the localization of stem cells to the infarct region or modulating local fibrosis signaling. The artificial blood pumping enhances the environment for myocardial tissue growth, such as by reducing wall stress and workload throughout the heart. Thus, both VAD and agent therapies are applied to control the remodeling process. The combined VAD and agent therapies include temporally coordinated VAD therapy delivery and agent therapy delivery, and not necessarily simultaneous or concurrent deliveries of both therapies. The agent delivery and the artificial blood pumping may be on a simultaneous, alternating, or any other coordinated basis designed for optimally modulating myocardial tissue growth. In the description of this system, an "agent" includes any one or more of the agents that are capable of directly or indirectly modulating myocardial tissue growth, including, but not being limited to, all such agents discussed in this document. The VAD, also known as cardiac-assist device, heart assist device, and artificial heart, includes a device physically coupled to the heart and/or the vascular system to aid a damaged or weakened heart in pumping blood, thereby reducing the workload of the heart and the stress on the cardiac walls. A "user" includes a physician or other caregiver treating a patient using the system providing for combined VAD and agent therapies.

FIG. 1 is an illustration of an embodiment of a system 100 that delivers the combined VAD and agent therapies and portions of an environment in which system 100 is used. System 100 includes an implantable system 115 and an external system 150. Implantable system 115 includes an implantable device 110 and a lead system 108. Implantable device 110 includes a VAD. In one embodiment, implantable device 110 is a VAD. The agent therapy is delivered using one or more injection instruments during and/or after the implantation of implantable device 110. In another embodiment, implantable device 110 combines a plurality of therapeutic devices, such as a VAD and an agent delivery device. The agent therapy is delivered partially or totally from implantable device 110. In one specific embodiment, the agent therapy is delivered using injection instruments during the implantation of implantable device 110 and delivered from implantable device 110 after the implantation. In another specific embodiment, after the implantation of implantable device 110, one or more agents are delivered from implantable device 110, and when necessary, another one or more agents are delivered with an injection instrument. As shown in FIG. 1, implantable device 110 is implanted in a body 102 and coupled to a heart 105 and/or the vascular system of body 102. In one embodiment, at least one lead of lead system 108 is a sensing lead that senses a cardiac signal indicative of whether heart 102 is in systole or diastole. In one embodiment, at least one lead of lead system 108 is an agent eluting lead that provides for delivery of one or more agents to heart 105. A telemetry link 140 provides for bidirectional communication between implantable device 110 and external system 150. In one embodiment, external system 150 is a medical device programmer. In another embodiment, external system 150 is a patient management system including an external device in the vicinity of implantable device 110, a remote device in a distant location, and a network providing for communications between the external device and the remote device. The remote device allows a user to monitor and treat patients from a remote location without the need for the patients' presence.

After the implantation, system 100 allows the delivery of the combined VAD and agent therapies to be controlled by implantable device 110 and/or external system 150. In one embodiment, implantable device 110 controls the delivery of the combined VAD and agent therapies based on a detected predetermined signal or condition. External system 150 controls the delivery of the combined VAD and agent therapies upon receiving an external user command. In a further embodiment, external system 150 automatically controls the delivery of the combined VAD and agent therapies by processing and analyzing signals and/or conditions detected by implantable device 110.

It is to be understood that while the VAD is a part of an implantable system in the embodiments specifically discussed in this document, the subject matter disclosed does not require implantability of the VAD. Any VAD that reduces the workload of the heart and the cardiac wall stress to various extents is usable for the combined VAD and agent therapies. VADs are generally discussed in, for example, Chandran et al., "Soft Tissue Replacements," in Bronzino (ed.), *The Biomedical Engineering Handbook*, 2$^{nd}$ ed., 1:43-11-13, (CRC Press, 2000), and Neuman, "Therapeutic and Prosthetic Devices," in Webster (ed.), *Medical Instrumentation: Application and Design*, 3$^{rd}$ ed., 597-600. VADs use various specific approaches to aid the heart to draw blood from the lungs through the pulmonary vein during diastole and pump the blood to the rest of the body through the aorta during systole. Specific examples of VADs are discussed in U.S. Pat. Nos. 5,139,517, 6,200,260, 6,299,575, 6,387,037, 6,390,969, 6,406,422, 6,428,464, 6,511,413, 6,530,876, 6,569,079, and 6,610,004, which are hereby incorporated by reference in their entirety.

Figure 2:
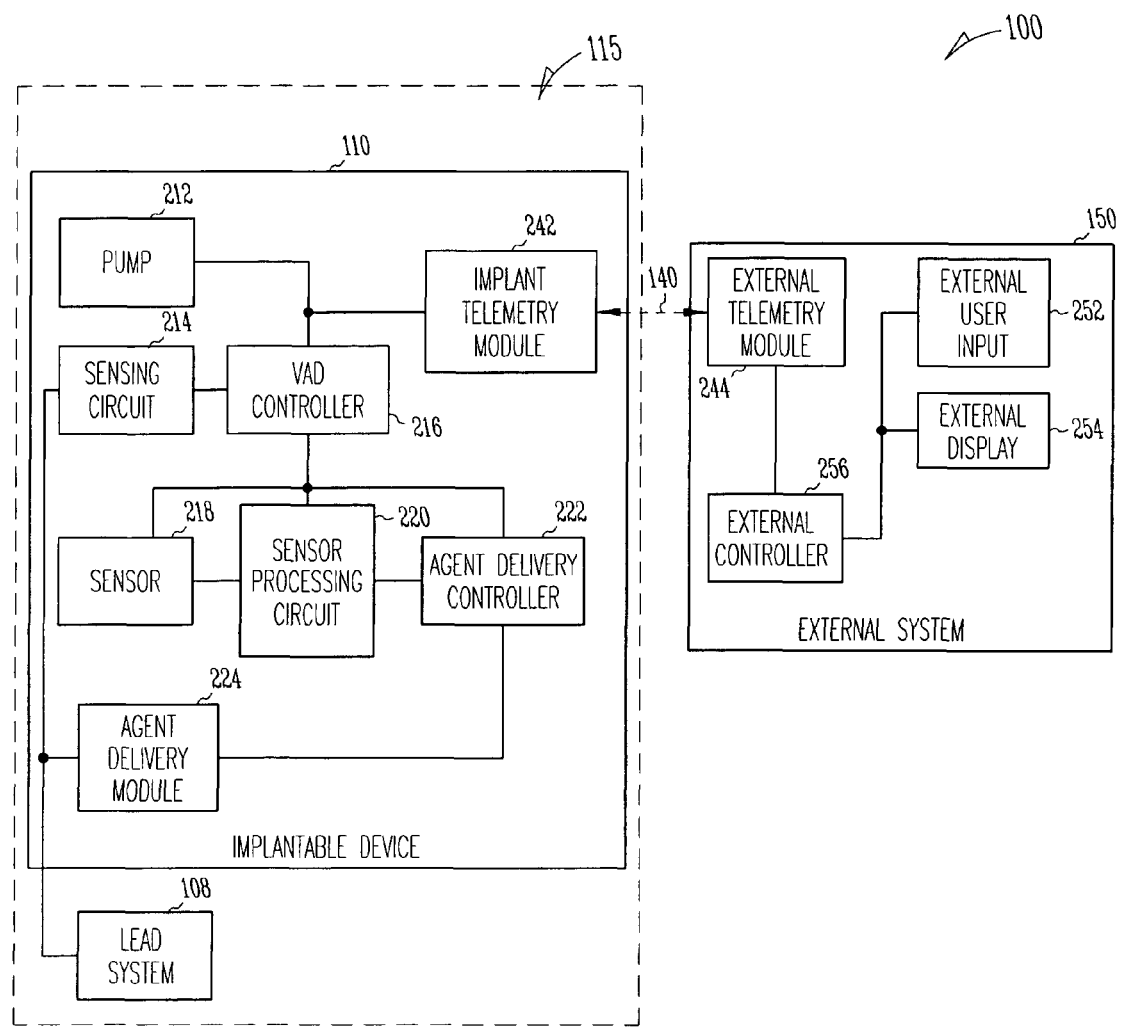
FIG. 2 is a block diagram showing one embodiment of the circuit of portions of the system of FIG. 1.

FIG. 2 is a block diagram showing one embodiment of the circuit of portions of the system 100. In this embodiment, implantable device 110 includes a VAD and an agent delivery device.

Implantable device 110 includes a pump 212, a sensing circuit 214, a VAD controller 216, a sensor 218, a sensor processing circuit 220, an agent delivery controller 222, and an agent delivery module 224. Pump 212 is a mechanical device that is coupled to heart 105 and/or the vascular system of body 102 to assist heart 105 in pumping blood. In one embodiment, pump 212 performs part of heart 105's pumping function. In another embodiment, pump 212 cyclically adjusts pressures in heart 105's chambers to facilitate blood pumping. Sensing circuit 214 senses one or more electrograms through one or more sensing leads of lead system 108. The one or more electrograms include events indicative of when heart 105 is in systole and diastole. VAD controller 216 controls pump 212 such that pump 212 and heart 105 perform substantially synchronized cyclic pumping. Sensor 218 senses one or more signals used to control the delivery of the combined VAD and agent therapies. Sensor processing circuit 220 processes the signal sensed by sensor 218 to produce one or more parameters indicative of a need for starting, stopping, or adjusting the agent delivery and/or the VAD operation. Agent delivery controller 222 produces an agent delivery control signal based on the parameters from sensor processing circuit 220 and the external user command. In one embodiment, the agent delivery control signal control the start, stop, and adjustment of the agent delivery. Agent delivery module 224 performs electrically controlled agent delivery by, for example, iontophoresis, electroporation, electrorepulsion, or electro-osmosis. In one embodiment agent delivery module 224 includes an agent reservoir to contain the agent and an agent eluting device to release the agent. In a further embodiment, agent delivery module 224 includes a reservoir agent level detector that monitors the amount of the agent remaining in the agent reservoir and produces an alert signal when the amount of the agent is below a predetermined level. The alert signal is transmitted to external system 150 to inform the user.

In one embodiment, sensor processing circuit 220 processes the signal sensed by sensor 218 before the signal is used by agent delivery controller 222 and/or VAD controller 216 to control the combined VAD and agent therapies. The one or more parameters produced by sensor processing circuit 220 include parameters measured and/or derived from the sensed signal. In one embodiment, sensor processing circuit 220 includes an event detector to detect one or more predetermined events indicative of a need to start, stop, or adjust the combined VAD and agent therapies. The one or more parameters produced by sensor processing circuit 220 include parameters indicative of the detection of the event and/or measured parameters associated with the detected event. In one specific embodiment, the event includes an abnormal cardiac condition. In one embodiment, sensor 218 includes a plurality of sensors to sense multiple signals used by agent delivery controller 222 and/or VAD controller 216 to control the combined VAD and agent therapies. Each of the multiple signals may be used by agent delivery controller 222 to control the agent therapy, by VAD controller 216 to control the VAD therapy, or by both controllers to control both the agent and VAD therapies. In one embodiment, if the event detector detects an abnormal cardiac condition that requires timely medical attention, implantable device 110 sends an alert signal to external system 150. In a further embodiment, implantable device 110 also sends one or more sensed signal segments indicative of the abnormal condition to external system 150.

In one embodiment, sensor 218 includes at least one electrogram sensing channel of sensing circuit 214, and sensor processing circuit 220 includes an even detector to detect an arrhythmia. In one embodiment, the event detector of sensor processing circuit 220 detects the arrhythmia by detecting heart rate and comparing the heart rate to one or more threshold rates. A bradycardia condition is detected when the heart rate falls below a bradycardia threshold. A tachycardia condition is detected when the heart rate exceeds a tachycardia threshold. In a further embodiment, the event detector of sensor processing circuit 220 detects the arrhythmia also by detecting morphological features of the electrogram to one or more predetermined templates. In one specific embodiment, the event detector of sensor processing circuit 220 includes an atrial fibrillation detector. In one specific embodiment, the event detector of sensor processing circuit 220 includes a ventricular fibrillation detector.

In one embodiment, sensor 218 senses a physiological signal indicative of ischemia, and sensor processing circuit 220 includes an ischemia detector. In one specific embodiment, sensor 218 senses an electrogram and the event detector of sensor processing circuit 220 runs an automatic ischemia detection algorithm to detect an ischemic condition from the electrogram. One specific example of an electrogram-based ischemia detector is discussed in Zhu et al., U.S. Pat. No. 7,340,303, entitled "EVOKED RESPONSE SENSING FOR ISCHEMIA DETECTION," assigned to Cardiac Pacemakers, Inc., which is incorporated herein by reference in its entirety. In another embodiment, sensor 218 includes an electrical impedance based sensor using a low carrier frequency (e.g. 100 Hz), and the ischemia detector runs an automatic ischemia detection algorithm to detect an ischemic condition from the electrical impedance signal. Tissue electrical impedance has been shown to increase significantly during ischemia, as discussed in Min, et al. International Journal of *Bioelectromagnetism*, 5(1): 53-56 (2003). Sensor 218 senses low frequency electrical impedance signal between electrodes interposed in the heart. The event ischemia detector detects the ischemia as abrupt changes in impedance (such as abrupt increases in value). In another specific embodiment, sensor 218 includes a local heart motion based sensor utilizing an accelerometer located within a lead body positioned on or in the heart, and the ischemia detector runs an automatic ischemia detection algorithm to detect an ischemic condition from the acceleration signal. The ischemia detector detects ischemia as an abrupt decrease in the amplitude of local cardiac accelerations.

In one embodiment, sensor 218 includes a metabolic sensor that senses a metabolic signal indicative of a cardiac metabolic level (rate of metabolism of cardiac cells). Examples of the metabolic sensor include a pH sensor, an oxygen pressure ($PO_2$) sensor, a carbon dioxide pressure ($PCO_2$) sensor, a glucose sensor, a creatine sensor, a C-creative protein sensor, a creatine kinase sensor, a creatine kinase-MB sensor, and any combination of such sensors. In one further embodiment, sensor processing circuit 220 includes an event detector to determine the cardiac metabolic level from the metabolic signal and compares the cardiac metabolic level to one or more predetermined thresholds defining a normal cardiac metabolic range. An abnormal condition, which may be indicative of an ischemic condition, is detected when the cardiac metabolic level is outside of the normal cardiac metabolic range.

In one embodiment, sensor 218 includes an implantable impedance sensor to measure pulmonary impedance, or impedance of a portion of the thoracic cavity. In a further embodiment, sensor processing circuit 220 includes an event detector to detect an abnormal condition when the impedance is out of its normal range. For example, pulmonary edema, i.e., fluid retention in the lungs resulting from the decreased cardiac output, increases the pulmonary or thoracic impedance. Thus, the abnormal condition may be indicative of decompensated heart failure. In one specific embodiment, the event detector produces the alert signal when the pulmonary or thoracic impedance exceeds a predetermined threshold impedance. In one embodiment, the impedance sensor is a respiratory sensor that senses the patient's minute ventilation. An example of an impedance sensor sensing minute ventilation is discussed in U.S. Pat. No. 6,459,929, "IMPLANTABLE CARDIAC RHYTHM MANAGEMENT DEVICE FOR ASSESSING STATUS OF CHF PATIENTS," assigned to Cardiac Pacemakers, Inc., which is incorporated herein by reference in its entirety.

In one embodiment, sensor 218 includes a pressure sensor. In a further embodiment, sensor processing circuit 220 includes an event detector to detect an abnormal condition when a pressure is outside of its normal range. The abnormal condition may be indicative of arrhythmias and/or heart failure that cause pressures in various portions of the cardiovascular system to deviate from their normal ranges. In one specific embodiment, sensor processing circuit 220 includes a systolic dysfunction detector to detect an abnormal condition related to pressure during the systolic phase of a cardiac cycle. In another specific embodiment, sensor processing circuit 220 includes a diastolic dysfunction detector to detect an abnormal condition related to pressure during the diastolic phase of a cardiac cycle. Examples of the pressure sensor include but are not limited to a left atrial (LA) pressure sensor, a left ventricular (LV) pressure sensor, an artery pressure sensor, and a pulmonary artery pressure sensor. Pulmonary edema results in elevated LA and pulmonary arterial pressures. A deteriorated LV results in decreased LV and arterial pressures. In various embodiments, the event detector of sensor processing circuit 220 detects an abnormal condition when the LA pressure exceeds a predetermined threshold LA pressure level, when the pulmonary arterial pressure exceeds a predetermined threshold pulmonary arterial pressure level, when the LV pressure falls below a predetermined threshold LV pressure level, and/or when the arterial pressure falls below a predetermined threshold LV pressure level. In other embodiments, sensor processing circuit 220 derives a parameter from one of these pressures, such as a rate of change of a pressure, and produces a signal when the parameter deviates from its normal range. In one embodiment, the LV pressure sensor senses the LV pressure indirectly, by sensing a signal having known or predictable relationships with the LV pressure during all or a portion of the cardiac cycle. Examples of such a signal include but are not limited to an LA pressure and a coronary vein pressure. One specific example of measuring the LV pressure using a coronary vein pressure sensor is discussed in U.S. Pat. No. 6,666,826, "METHOD AND APPARATUS FOR MEASURING LEFT VENTRICULAR PRESSURE," assigned to Cardiac Pacemakers, Inc., which is hereby incorporated by reference in its entirety.

In one embodiment, sensor 218 includes a cardiac output or stroke volume sensor. Examples of stroke volume sensing are discussed in U.S. Pat. No. 4,686,987, "BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND," and U.S. Pat. No. 5,284,136, "DUAL INDIFFERENT ELECTRODE PACEMAKER," both assigned to Cardiac Pacemakers, Inc., which are incorporated herein by reference in their entirety. In a further embodiment, sensor processing circuit 220 includes an event detector to detect an abnormal condition when the stroke volume falls below a predetermined threshold level. The abnormal condition may be indicative of decompensated heart failure.

In one embodiment, sensor 218 includes a neural activity sensor to detect activities of the sympathetic nerve and/or the parasympathetic nerve. A significant decrease in cardiac output immediately stimulates sympathetic activities, as the autonomic nervous system attempts to compensate for deteriorated cardiac function. In one specific embodiment, the neural activity sensor includes a neurohormone sensor to sense a hormone level of the sympathetic nerve and/or the parasympathetic nerve. In a further embodiment, sensor processing circuit 220 includes an event detector to detect an abnormal condition when the hormone level exceeds a predetermined threshold level. In another specific embodiment, the neural activity sensor includes an action potential recorder to sense the electrical activities in the sympathetic nerve and/or the parasympathetic nerve. In a further embodiment, sensor processing circuit 220 includes an event detector to detect the abnormal condition when the frequency of the electrical activities in the sympathetic nerve exceeds a predetermined threshold level. Examples of direct and indirect neural activity sensing are discussed in U.S. Pat. No. 5,042,497, "ARRHYTHMIA PREDICTION AND PREVENTION FOR IMPLANTED DEVICES," assigned to Cardiac Pacemakers, Inc., which is hereby incorporated by reference in its entirety. The abnormal condition may be indicative of heart failure.

In one embodiment, sensor 218 includes a heart rate variability detector. An example of detecting the heart rate variability is discussed in U.S. Pat. No. 5,603,331, "DATA LOGGING SYSTEM FOR IMPLANTABLE CARDIAC DEVICE," assigned to Cardiac Pacemakers, Inc., which is incorporated herein by reference in their entirety. In a further embodiment, sensor processing circuit 220 includes an event detector to detect the abnormal condition when the heart rate variability falls below a predetermined threshold level. The abnormal condition may be indicative of decompensated heart failure.

In one embodiment, sensor 218 includes a renal function sensor. Decompensated heart failure results in peripheral edema primarily because of fluid retention of the kidneys that follows the reduction in cardiac output. The fluid retention is associated with reduced renal output, decreased glomerular filtration, and formation of angiotensin. Thus, in one specific embodiment, the renal function sensor includes a renal output sensor to sense a signal indicative of the renal output. In a further embodiment, sensor processing circuit 220 includes an event detector to detect an abnormal condition when the sensed renal output falls below a predetermined threshold. In another specific embodiment, the renal function sensor includes a filtration rate sensor to sense a signal indicative of the glomerular filtration rate. In a further embodiment, sensor processing circuit 220 includes an event detector to detect an abnormal condition when the sensed glomerular filtration rate falls below a predetermined threshold. In yet another specific embodiment, the renal function sensor includes a chemical sensor to sense a signal indicative of angiotensin II levels. In a further embodiment, sensor processing circuit 220 includes an event detector to detect an abnormal condition when the sensed angiotensin II levels exceed a predetermined threshold level. Such abnormal conditions may be indicative of decompensated heart failure.

In one embodiment, sensor 218 includes an acoustic sensor being a heart sound sensor and/or a respiratory sound sensor. Arrhythmias and/or heart failure cause abnormal cardiac and pulmonary activity patterns and hence, deviation of heart sounds and respiratory sounds from their normal ranges of pattern and/or amplitude. In a further embodiment, sensor processing circuit 220 includes an event detector to detect an abnormal condition when the heart sound or respiratory sound is out of its normal range. For example, detection of the third heard sound (S3) is known to indicate heart failure. In one specific embodiment, sensor processing circuit 220 includes an event detector to detect an abnormal condition when the S3 amplitude or activity exceeds a predetermined threshold level.

In one embodiment, sensor 218 includes a displacement sensor to sense a signal indicative of a strain of myocardial tissue. After MI, myocardial tissue in the infract region becomes less elastic due to the scar formation process. By modulating myocardial tissue growth, the agent therapy reduces the scar formation and promotes myocardial tissue replacement, thus reducing the loss of the elasticity and/or restores it. Therefore, the strain of myocardial tissue is indicative of a need for the therapy as well as the results of the therapy. In a further embodiment, sensor processing circuit 220 includes an event detector to detect an abnormal condition when the sensed strain of myocardial tissue falls below a predetermined threshold. The abnormal condition is indicative of a degree of myocardial tissue scar formation.

In one embodiment, sensor 218 includes a remodeling sensor to sense a signal indicative a degree of myocardial remodeling. In one specific embodiment, the remodeling sensor includes two or more piezoelectric crystals incorporated in one or more leads of lead system 108 to sense a size of an injured myocardial region such as an infarct region. The size of the injured myocardial region is estimated based on spatial information sensed by the crystals and averaged over a predetermined period of time. In one embodiment, a substantial degree of change in the size of the injured region indicates a need to start, stop, or adjust the combined electrical and agent therapies. In another specific embodiment, sensor 212 includes a hypertrophic sensor to sense a signal indicative of a degree of myocardial hypertrophy, which indicates the progress of the remodeling process. In another specific embodiment, sensor 218 includes a chemical sensor to sense the change in expression or concentration of Endothelin-1 (ET-1), BNP, or p38MAPK, which are known to change during hypertrophy response. In a further embodiment, sensor processing circuit 220 includes an event detector to detect an abnormal condition when the degree of myocardial remodeling exceeds a predetermined threshold. The degree of myocardial remodeling is represented by one or more of the degree of change in the size of the injured region, the degree of myocardial hypertrophy, and the degree of the change in expression or concentration of Endothelin-1 (ET-1), BNP, or p38MAPK.

In one embodiment, sensor 218 includes a thermal sensor to sense a signal indicative of a perfusion of thermal energy in myocardial tissue. In one specific embodiment, the thermal sensor includes a thermal energy source to heat or cool at least a portion of the myocardial tissue including the infract region, a temperature sensor to sense the temperature in the infarct region, and a perfusion calculator to calculate the rate of change in the temperature in the infarct region. The ability of myocardial tissue to perfuse thermal energy reduces with the post MI scar formation process. Therefore, the rate of change in the temperature, as a measure of thermal perfusion, is indicative of a need for the therapy as well as the results of the therapy. In a further embodiment, sensor processing circuit 220 includes an event detector to detect an abnormal condition when the rate of change in the temperature falls below a predetermined threshold. This abnormal condition is indicative of a degree of myocardial tissue scar formation.

Embodiments of sensor 218 and the event detector of sensor processing circuit 220 are discussed in this document by way of example, but not by way of limitation. In various embodiments, sensor 218 and the event detector of sensor processing circuit 220 may include combinations of various sensors and detectors discussed above. Other methods and sensors for directly or indirectly detecting an abnormal cardiac condition demanding the start, stop, or adjustment of the combined VAD and agent therapies are also usable by system 100. In further embodiments, sensor 218 also includes sensors to sense signals not directly used to control the operation of implantable device 110, but usable for diagnostic and other therapeutic purposes.

Implantable device 110 includes a hermetically sealed metal can to house at least portions of the device. In one embodiment, sensor 218 resides within the metal can. In another embodiment, sensor 218 is outside of the metal can. In one embodiment, sensor 218 is incorporated into lead system 108.

Lead system 108 includes one or more sensing leads allowing sensing of electrical signals from heart 105. In one embodiment, lead system 108 includes one or more transvenous leads each having at least one sensing electrode placed within heart 105. In one embodiment, lead system 108 includes one or more epicardial leads each having at least one sensing electrode attached to the epicardial wall of heart 105. Lead system 108 includes at least one agent eluting lead connected to agent delivery module 224. In one embodiment, the agent eluting lead includes a fluid passageway having one opening at one end of the lead connected to the agent reservoir of agent delivery module 224 and another opening connected to an agent eluting electrode at or near the other end of the lead that is to be disposed in or about heart 105. The fluid passageway allows fluid communication between implant agent reservoir 224 and the location to which the agent is released. Thus, lead system 108 allows sensing of electrical signals from heart 105 and delivery of the agent to heart 105. In one embodiment, lead system 108 includes an endocardial lead including at least one agent eluting electrode configured to be disposed within one of a coronary sinus and a portion of a great cardiac vein adjacent to the left ventricle of heart 105. In another embodiment, lead system 108 includes an epicardial lead including at least one agent eluting electrode configured to be attached to a portion of an epicardial wall of heart 105. In one embodiment, sensor 218 is built-in or attached to a lead of lead system 108, such that when the lead is implanted, sensor 218 is in a blood pool.

External system 150 includes an external user input 252, an external display 254, an external device controller 256, and external telemetry module 244. External user input 252 receives the external user command controlling the combined VAD and agent therapies from the user. In a further embodiment, it also receives other commands or instructions to control the operation implantable device 110. External system 150 transmits the external user command to implantable device 110, resulting in a production of the agent delivery control signal by agent delivery controller 222. External controller 256 controls the overall operation of external system 150. In one embodiment, external controller 256 generates commands controlling implantable device 110 based on the external user command. In one embodiment, external controller 256 generates commands controlling implantable device 110 based on the external user command and signals acquired by sensor 218 and transmitted to external system 150 via telemetry link 140. In one embodiment, external controller 256 executes an automatic algorithm to control the combined VAD and agent therapies based on the signals acquired by sensor 218, such as when the user is not immediately available. External telemetry module 244 provides for a telemetry interface allowing external device 150 to communicate with implantable device 110 via telemetry link 140. In one embodiment, external system 150 is a medical device programmer containing external user input 252, external display 254, external device controller 256, and external telemetry module 244. In another embodiment, external system 150 includes an external device wirelessly coupled to implantable device 110, a remote device in a remote care facility. The external device and the remote device are linked through a telecommunication network. The distribution of external user input 252, external display 254, and external device controller 256 within external system 150 depends on practical needs in providing efficient patient care. In one embodiment, the external device includes external user input 252, such that the user can enter the external user command at the patient's presence. In another embodiment, the remote device includes external user input 252, such that the user can enter the external user command without the patient's presence. In another embodiment, the external device and the remote device each include an user input device to receive the external user command.

Telemetry link 140 is a wireless bidirectional data transmission link supported by implant telemetry module 242 and external telemetry module 244. In one embodiment, telemetry link 140 is an inductive couple formed when two coils—one connected to implant telemetry module 242 and the other connected to external telemetry module 244—are placed near each other. In another embodiment, telemetry link 140 is a far-field radio-frequency telemetry link allowing implantable device 110 and external device 252 to communicate over a telemetry range that is at least ten feet.

Figure 3:
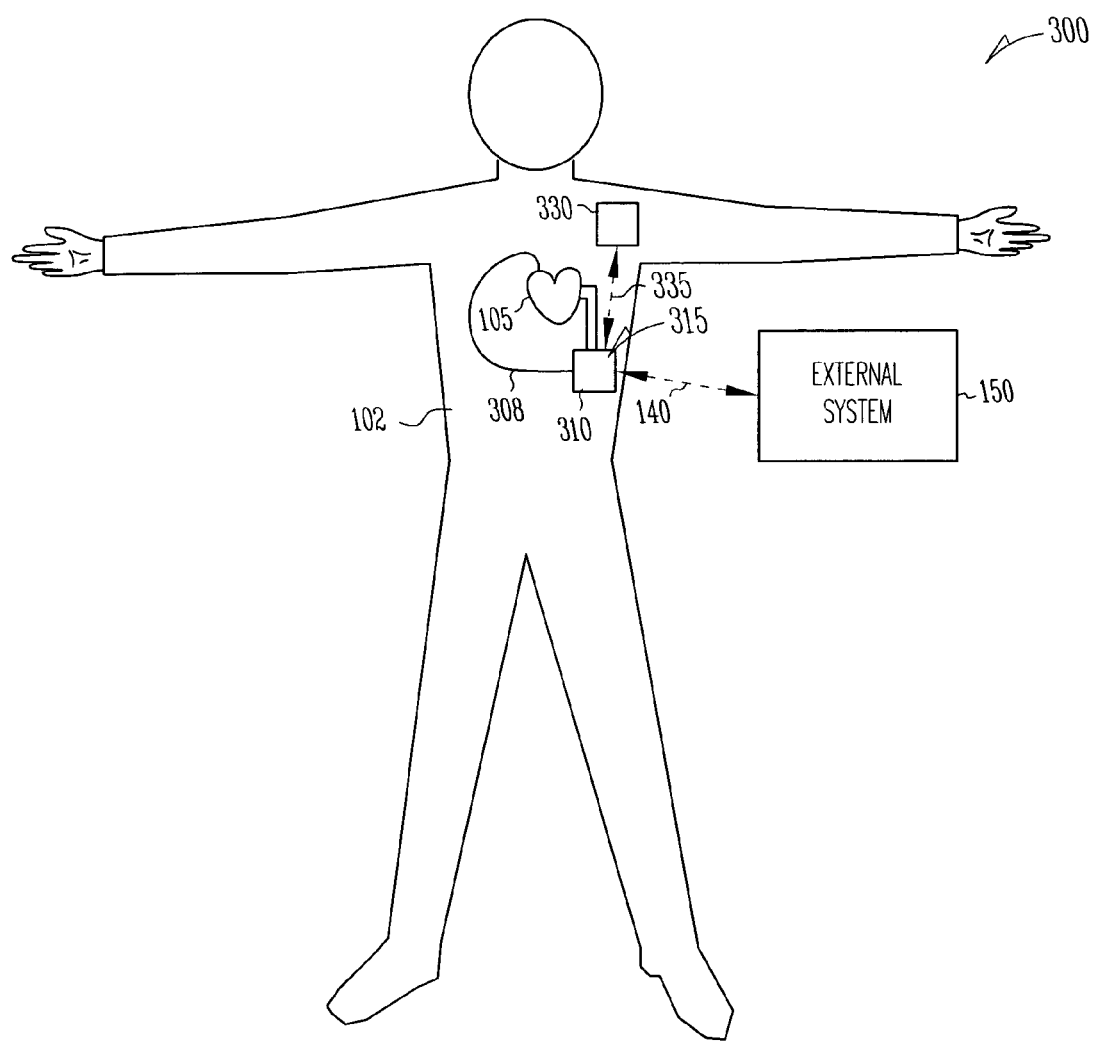
FIG. 3 is an illustration of an embodiment of another system delivering combined VAD and agent therapies to a heart and portions of an environment in which the system is used.

FIG. 3 is an illustration of an embodiment of another system 300 delivering the combined VAD and agent therapies a heart and portions of an environment in which it is used. System 300 includes an implantable VAD 310, an implantable agent delivery device 330, and a communication link 335 coupled between the two devices. Lead system 308 provides for one or more electrical connections between implantable VAD 310 and heart 105 through which at least one electrogram is sensed to indicate which heart 105 is in systole or diastole. Identical numerals appearing in both FIGS. 1 and 3 indicate corresponding system components included in systems 100 and 300 that are substantially identical. In one embodiment, system 300 differs from system 100 by having the agent delivery device physically separate from the VAD.

System 300 allows the delivery of the combined VAD and agent therapies to be controlled by any one of implantable VAD 310 and external system 150. In one embodiment, implantable VAD 310 controls the delivery of the combined VAD and agent therapies based on a detected predetermined signal or condition. External system 150 controls the delivery of the combined VAD and agent therapies upon receiving an external user command. In a further embodiment, external system 150 automatically controls the delivery of the combined VAD and agent therapies by processing and analyzing signals and/or conditions detected by implantable VAD 310.

Figure 4:
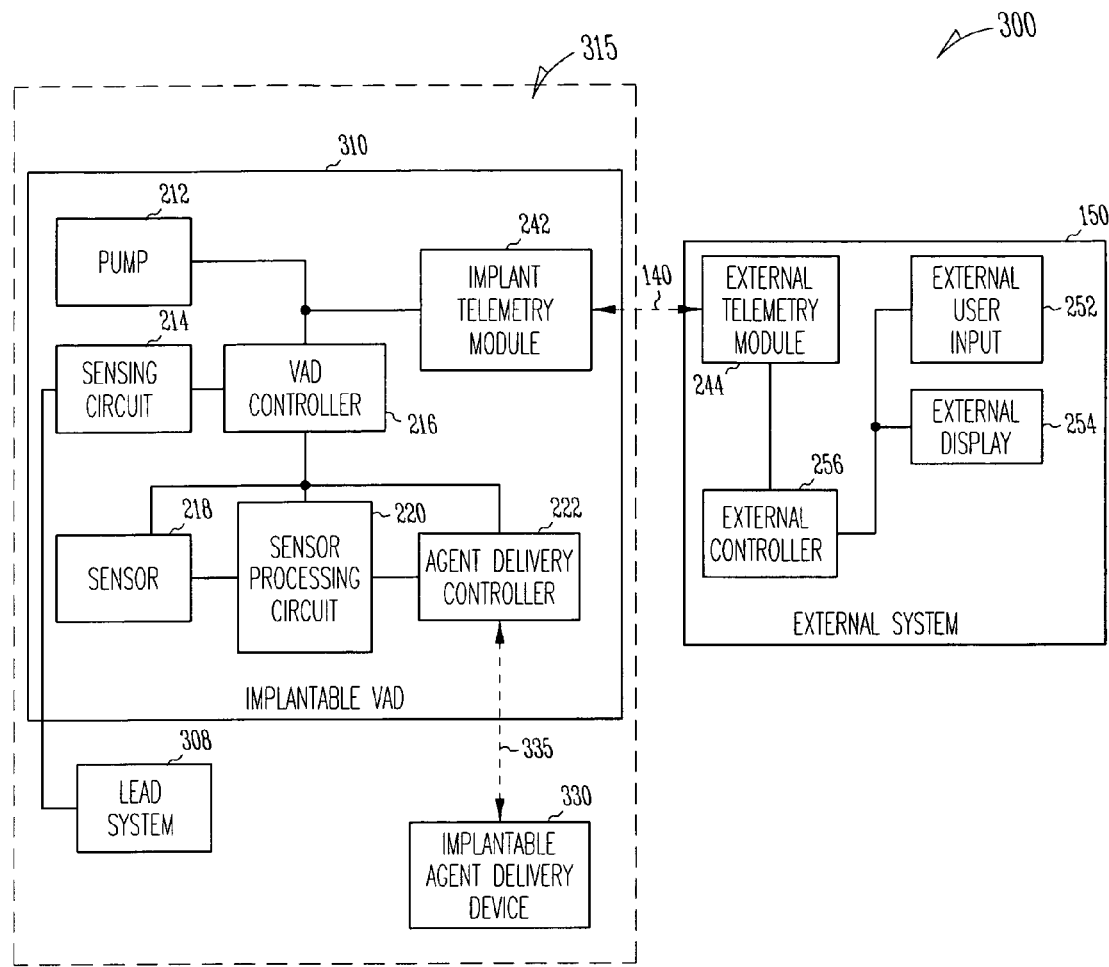
FIG. 4 is a block diagram showing one embodiment of the circuit of portions of the system of FIG. 3.

FIG. 4 is a block diagram showing one embodiment of the circuit of portions of system 300. Identical numerals appearing in both FIGS. 2 and 4 indicate corresponding system components included in systems 100 and 300 that are substantially identical. In general, implantable VAD 310 retains, among other components, pump 212, sensing circuit 214, VAD controller 216, sensor 218, sensor processing circuit 220, agent delivery controller 222, and implant telemetry module 242 of implantable device 110. Agent delivery module 224 of implantable device 110 is replaced by a separate implantable device, that is, implantable agent delivery device 330.

Implantable agent delivery device 330 performs electrically controlled agent delivery by, for example, iontophoresis, electroporation, electrorepulsion, or electroosmosis. In one embodiment, implantable agent delivery device 330 includes an agent reservoir to contain the agent and an agent eluting device to release the agent. In one embodiment, the agent eluting device includes at least one electrode connected to the agent reservoir. In one specific embodiment, implantable agent delivery device 330 includes a polymer matrix providing for electrically-controlled agent delivery by iontophoresis. Agent delivery controller 222 generates a signal causing an electrical field to be applied on the polymer matrix. The rate of agent release is controlled by the strength of the electric field. In one embodiment, the electric field is created in tissue surrounding implantable agent delivery device 330 through electrodes placed in the vicinity of implantable agent delivery device 330. In another embodiment, a wired connection between implantable VAD 310 and implantable agent delivery device 330 allows electrical field to be created upon the polymer matrix applying a voltage across it. In one embodiment, the agent eluting device is attached to an organ of body 102 to allow the agent to be released to the tissue of that organ. In one specific embodiment, implantable agent delivery device 330 is constructed as an agent eluting epicardial patch for attachment onto the epicardial wall of heart 105. In another embodiment, the agent eluting device is disposed in blood to allow the agent to be released to the blood. In one specific embodiment, implantable agent delivery device 330 is incorporated into another implantable device (other than implantable VAD 310), such as a coronary stent, a lead of lead system 308, or other devices implanted in or about the heart or the vascular system. In a further embodiment, where communication link 335 provides for bidirectional communication, implantable agent delivery device 330 includes a reservoir agent level detector to monitor the amount of the agent remaining in the agent reservoir and produces an alert signal when the amount of the agent is below a predetermined level. The alert signal is transmitted to implantable VAD 310. Implantable VAD 310 relies the signal to external system 150 to inform the user.

Figure 5:
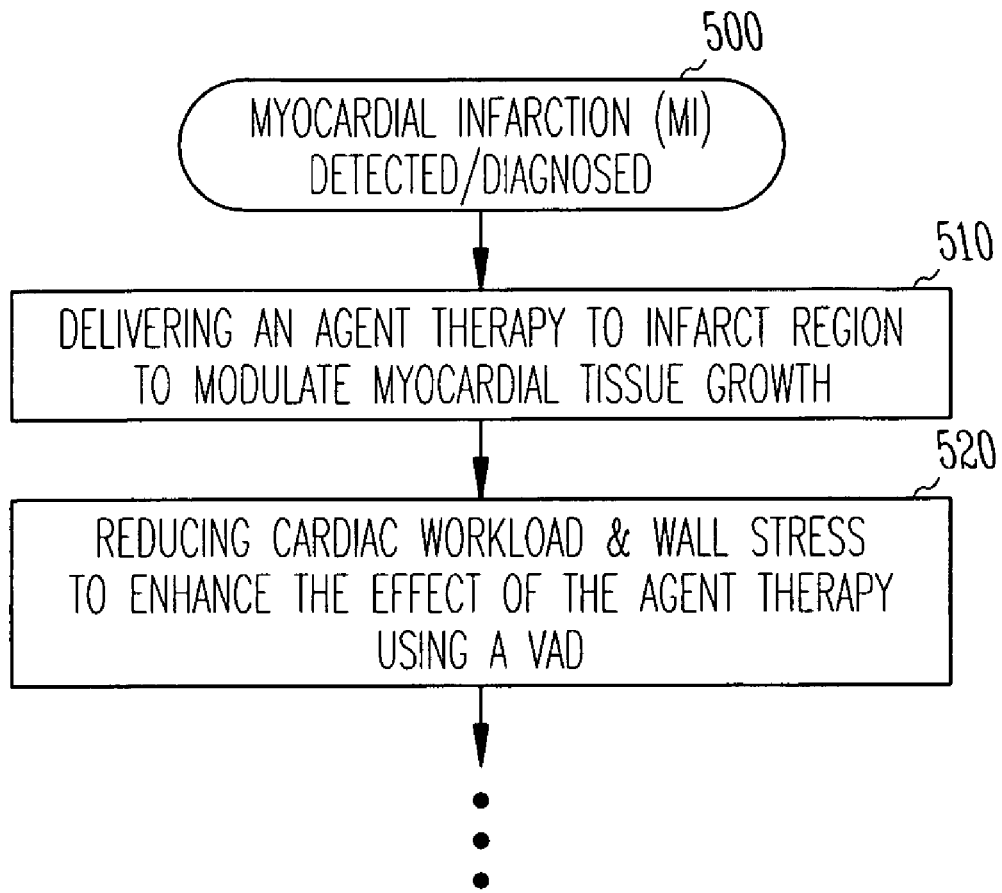
FIG. 5 is a flow chart illustrating a method for delivering combined VAD and agent therapies.

FIG. 5 is a flow chart illustrating a method for delivering the combined VAD and agent therapies. In response to a detection or diagnosis of MI at 500, an agent therapy is delivered to the infarct region(s) of the myocardium to modulate myocardial tissue growth at 510, and cardiac workload and wall stress are reduced, by using a VAD, to enhance the effects of the agent therapy at 520. The flow chart of FIG. 5 is not intended to limit or suggest any particular order by which the agent therapy and the VAD therapy are delivered. Steps 510 and 520 may be performed, and either of both of the steps may be repeated, in any predetermined order or sequence. In one embodiment, the agent therapy and the VAD therapy are temporally coordinated based on a patient's overall cardiac conditions, such as degree of post MI remodeling, degree of scar formation, and hemodynamic performance. Because such cardiac conditions change over time, the agent therapy and the VAD therapy are adjusted on an ongoing basis. The adjustment may include temporal coordination of the agent therapy and the VAD therapy, adjustment of VAD workload, and/or adjustment of amount and content of the agent.

In one embodiment, one or more agents are delivered to a cardiac region including at least portions of the infarct region in an amount effective to modulate myocardial tissue growth. VAD operates to enhance one or more effects of the agent in modulating the myocardial tissue growth by reducing the cardiac wall stress. In one embodiment, the agent and VAD therapies are delivered by using selected or all the functions provided by system 100, as discussed above. In another embodiment, the agent and VAD therapies are delivered by using selected or all the functions provided by system 300, as discussed above. The embodiments discussed in this document may be combined, other embodiments may be utilized, and/or structural, logical and electrical changes may be made, without departing from the scope of the present invention.

Agents Useful in the Apparatus and Methods of the Invention

In one embodiment, agents within the scope of the present subject matter include, but are not limited to, those which localize stem cells to areas of tissue damage, e.g., myocardial damage, or otherwise modulate tissue growth, e.g., increase vascularization (angiogenesis in the heart), reduce adverse remodeling, modulate fibrosis signaling, enhance stem cell proliferation, enhance cardiomyocyte proliferation, modulate myofibroblast proliferation, or any combination thereof. Those agents including beta-blockers, angiotensin converting enzyme (ACE) inhibitors, and angiotensin receptor blockers, which are delivered by the device of the invention, may be employed alone or in conjunction with other pharmaceutical agents, such as anti-hypertensive agents, anti-arrhythmic agents, pressors, vasopressors, vasodilators, anti-hyperlipidemic agents, anti-anginal agents, ionotropic agents, diuretics, volume expanders, thrombolytics, anti-platelet agents, beta-blockers, ACE inhibitors, and angiotensin receptor blockers, or any combination thereof, which are locally delivered by a device other than a device of the invention or systemically delivered.

In one embodiment, an agent for use in the systems and methods of the invention includes but is not limited to a cytokine, e.g., a cytokine including but not limited to, γIP10, 4-1BBL, 6Ckine, activin, amphiregulan, angiostatin, Apo2L, APRIL, BAFF, ENA-78, eotaxin-1, eotaxin-2, eotaxin-3, EGF, FGF, e.g., bFGF, FGF-8b or FGF-2, FasL, G-CSF, GM-CSF, Gro-α, Gro-β, Gro-γ, HCC-1, HCC-4, HGF, IFNα, IFNβ, IGF-I, IGF-II, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, LARC, MCP-1, MCP-2, MCP-3, MCP-4, MCP-5, MEC, MIF, MIG, MIP1α, MIP1β, NGF, PDGF, RANTES, SCF, SDF-1, TARC, TGF-α, TGF-β or TPO, or an inhibitor thereof, e.g., ouabain, amlodipine, pentaxifylline, amiodarone, SR33589 or ATI-2001 (Kodama, *Cardiovas. Res.*, 35:13 (1997)), adenosine, VEGF such as VEGF-E (Kibu et al., *BBRC*, 301:371 (2003)), $VEGF_{165}$, or $VEGF_{121}$, NOS, retinoic acid, glycolic acid, angiopoietins, 12-LOX, hydrazones, IGF, cyanomethyl substituted thiazoliums (U.S. Pat. No. 6,610,716), imidazoliums, azolium chroman (U.S. Pat. No. 6,596,745), thiazole (U.S. published application 2002/0022022), imidazole, matrix metallo-proteinases (MMPs) such as MMP-1, 2, 9 or 13, pentafluorosulfanylbenzoyl guanidines (U.S. published application 2003/0216476), AT1 receptor antagonists such as candesartan, inhibitors of MEK or P13-K, PD 098059 or LY294002 (see Hafizi et al., *Cir. Exp. Pharma Physiol.*, 26:511 (1999), ACE inhibitors such as enalapril, cilazapril, enalaprilat, omapatrilat, lisinopril, ramipril, captopril, furosemide, or trandopril, adrenomedullin, pyridoxalbenzoyl hydrozone analogs (U.S. Pat. No. 6,005, 009), sulfonamidocarbonyl pyridine-2-carboxamides and pyridine-n-oxides (U.S. Pat. No. 5,610,172), asporin (U.S. published application 2003/30148351), dextran sulfate, pentosan polysulfate, IL-6R inhibitors, leukemia inhibitor factor (LIF), cyclin D2, angiotensin receptor antagonists, e.g., losartan, proangiogenic agents, e.g., those which promote vascularization, such as IGF, EGF, G-CSF, GMCSF, HGF, proliferin, and angiotropin, angiopoietins, e.g., Ang-1, P1GF (placental GF), polysaccharides, HMG-CoA reductase inhibitors, e.g., statins, agents which modulate fibrosis, e.g., TGF-β or inhibitors thereof, e.g., decorin, or TGF-β receptor antagonists, β-adrenergic antagonists, e.g., α-receptor antagonists such as propanolol, metaprolol, carvediol, bunazosin, or isoprenaline, lacidipine, L-type/C-type calcium channel blockers, e.g., mibefradine, L-type calcium channel blockers, e.g., nifedipine, vasodilators, endothelin antagonists, such as endothelin A or B receptor inhibitors, e.g., BQ-123 or BQ788 (Higashi et al., *Br. J. Pharmacol.*, 121:782 (1997)), bosentan, as well as modulators of prolyl-4-hydroxylase (P4H), matrix metalloproteinases, TGF-β, PDGF, EGF, TGF-α, bFGF, IGF, IL-1, TNF-α, e.g., etanercept, tissue inhibitor of metalloproteinase (TIMP), catecholamines, steroids, retinoids, parathyroid hormones, or glucocorticoids, aldosterone, or antagonists thereof, e.g., spironolactone, bradykininase inhibitors, HOE 140 (Villareal et al., *Basic Res. Cardiol.*, 93 Supp 3:4 (1998)), chymase inhibitors, e.g., NK3201 (Sukenaga et al., *Jap. J. Pharmacol.*, 90:218 (2002)), adriamycin, phenyloin, tanshinone VI (Yagi, *J. Pharm. Soc. Japan,* 123:517 (2003), SB203680 (Akiyama-Uchida et al., *Hypertension,* 40:148 (2002), or a calcineurin inhibitor, e.g., FK506.

In particular, to modulate fibrosis, one or more of the following agents may be employed: MEK inhibitors, e.g., PD098059 or LY294002, aldosterone antagonists, chymase inhibitor, e.g., chymostatin or NK3201, tanshinone VI, beta-blockers, such as metoprolol or carvediol, ACE inhibitors, e.g., enalapril, enalaprilat, or cilazapril, calcineurin modulators, e.g., calcineurin inhibitors, beta-blockers, such as metoprolol or carvediol, bradykinin modulators, HGF, modulators of P4H, MMP, TGF-β, PDGF, EGF, TGF-α, bFGF, IGF, IL-1, TNF-α, retinoids, catecholamines, steroids, parathyroid hormone or glucocorticoids; BB-94 (Bigatel et al., *J. Vasc. Surg.*, 29:130 (1999)), pentafluoro sulfanyl benzoyl guanidines, selective AT1 receptor antagonists, phenoxytoin, or modulators of endothelin. In one embodiment, the agent modulates fibroblast proliferation and/or extracellular matrix synthesis or degradation, e.g., by modulating MMPs and TIMP, e.g., TIMP type 1, 2, 3 or 4.

To treat heart failure, one or more of the following agents may be employed: beta-blockers, such as metoprolol or carvediol, ACE inhibitors, e.g., enalapril, enalaprilat, or cilazapril, aldosterone antagonists, endothelin receptor antagonists, TNF-α inhibitors, e.g., etanercept, matrix metalloproteinase inhibitors, vasodilators, β-adrenergic antagonists, angiotensin receptor blockers, e.g., losartan or anomethyl substituted thiaxoliums, imidazoliums, thiaxoles, imidazole, oxazole, pentoxifylline, thalidomide, intravenous immunoglobulin, IL-6, IL-10, IL receptor antagonists, TNF or chemokine modulators.

To treat remodeling, one or more of the following agents may be employed: beta-blockers, such as metoprolol or carvediol, ACE inhibitors, e.g., enalapril, enalaprilat, or cilazapril, aldosterone antagonists, organic nitrites, hydralazine, ramipril, furosemide, a calcium channel blocker, e.g., amlodipine, statins, vasodilators, propranolol, metaprolol, bunazosin, omapatrilat, isoproterenol, endothelin receptor inhibitors, aldosterone antagonists, e.g., spirolactone, AT1 receptor antagonists, bradykinase inhibitors, chymase inhibitors, retinoids, adriamycin, phenoxytoin, adrenomedullin, IL-6R inhibitors, cytokinases, lacidipine, a L-type/C-type calcium channel blocker, e.g., mibefradil, a L-type calcium channel blocker, e.g., nifedipine, or TGF-β inhibitors.

To enhance vasodilation, one or more of the following agents may be employed: EGF, IGF, HGF, proliferin, angiotropin, VEGF, angiopoietin, FGF, SDF-1, P1GF, SCF, IL-8, polysaccharides, HMG-COA reductase inhibitors, NOS, TGF-β, retinoic acid, or a hydrazone (U.S. Pat. No. 6,660,737).

To enhance cardiomyocyte proliferation, one or more of the following agents may be employed: G-CSF, GM-CSF, SDF, IGF, HGF, IL-8, angiotensinogen, or angiotensin type 1 or 2 receptor antagonists.

The present agents may be employed with other agents including but not limited to diuretics such as thiazides, e.g., hydrochlorothizide, loop diuretics, e.g., furosemide, and potassium-sparing agents, e.g., amiloride, spironolactone and triamterene and hydrochlorothiazide, beta-blockers such as bisoprolol, carvedilol, labetolol and metoprolol, angiotensin-converting enzyme inhibitors such as benazepril, captopril, enalapril, fosinopril, lisinopril, perindopril, quinapril, ramipril, trandolapril, delapril, pentopril, moexipril, spirapril, temocapril, and imidapril, calcium channel blockers, alpha blockers, angiotensin II antagonists, e.g., losartan, statins, e.g., atorvastatin, pitavastatin, and pravastatin, or other lipid lowering agents, moxonidine, dihydropyridines, e.g., amlodipine, class III and IV antiarrhythmics, e.g., amiodarone, azimilide, sotalol, dofetilide, and ubutilide, aspirin, selective non-adrenergic imidazoline receptor inhibitors, hebivolol, vasopeptidase inhibitors, e.g., fasidotritat, omapatrilat, samapatrilat, substrates, inhibitors or inducers of cytochrome P450 enzymes, lidocaine, warfarin, oligonucleotides (sense or antisense), natriuretic peptides such as ANP, BNP, NT pro BNP, CNP, and DNP, colforsin daropate hydrochloride (forskilin derivative), antagonists of platelet integrin IIb/IIIa receptors, e.g., abciximab and trofiblant, reteplase, P2 receptor antagonists, e.g., ticlopidine and clopidrogel, mibefradil, hirudin, acetylcholinesterase inhibitors, cardiac glycosides, e.g., digoxin and digitoxin, bradykinin, neutral endopeptidease inhibitors, e.g., neprilysin, direct-acting vasodilators, e.g., hydralazine, nitroglycerin, sodium nitroprusside, catecholamines, dobutramine, dopamine, phosphodiesterase inhibitors, e.g., amrinone and milrinone, TNFα, pentoxifylline, growth hormone, cytokine inhibitors, aldosterone receptor antagonists, calcium sensitizers, nesiritide, 3,5-dicodothyropropionic acid, etomoxir, endothelin receptor antagonists, chlorthiadone, doxazosin, nesiritide, cilostazol, rilmenidine, ticlopidine, dihydropines such as nifedipine and nisoldipine, timolol, propanolol, verapamil, diltiazem, lisinopril, noopept (N-phenylacetyl-L-polyglycine ethylester), cariporide, geldanamycin, radicicol, ibudilast, selective delta (1) agonists such as 2-methyl-4a-alpha-(3-hydroxy-phenyl)-1,2,3,4, 4a,5,12,12a-alpha-octahydroquinolinol [2,3,3-g]isoquinoline, monophosphoryl lipid A, RC552, adenosine, adenosine receptor agonists, adenosine triphosphate sensitive channel openers, dipyridamole, fibroblast growth factor, atenolol, ezetimibe, lerosimendan, sirolimus, paclitaxil, actinomycin D, dexamethasone, tacrolimus, everolimus, estradiol, quinapril, tranilast, antiopeptin, trapidil, lacidipine, thiazolidinediones, fenofibrate, lacidipine, nebrivolol, nicotinic acid, probucal, rosuvastatin, gemfibrozil, glitazones, indobugen, alpha-tocopherol, dypiridamole, resins, e.g., cholestyramine and colestipol, bezafibrate, or listat, niacin, heparin, e.g., low molecular weight heparins such as dalteparin sodium and nadroparin calcium, bivalirucin, nitroglycerin, nicorandil, denopamine, eptifibatide, xemilofiban, bofiban, trimetazidine, nicorandil, dalteparin, and isosorbide 5-mononitrate. Additional pharmaceutical agents may be considered based on evidence of their direct or indirect roles in preventing or reducing injury or hemodynamic compromise related to myocardial infarction and/or heart failure. Examples of such pharmaceutical agents include, but are not limited to, L-arginine; nitric oxide (NO); NO derivatives such as nitroxl anion (HNONO—) and peroxynitrite (ONOO—); iNOS, eNOS, and inhibitors such as nitro-L-arginine methyl ester; NO donors such as diethylamine (DEA) NO and nitroglycerin (NTG); and interleukins and interleukin inhibitors.

Sources of Donor Cells for Cell-Based Therapies

Sources for donor cells in cell-based therapies include skeletal muscle derived cells, for instance, skeletal muscle cells and skeletal myoblasts; cardiac derived cells, myocytes, e.g., ventricular myocytes, atrial myocytes, SA nodal myocytes, AV nodal myocytes, and Purkinje cells; bone marrow-derived cells, e.g., mesenchymal cells and stromal cells; smooth muscle cells; fibroblasts; SP cells; or pluripotent cells or totipotent cells, e.g., teratoma cells, hematopoietic stem cells, for instance, cells from cord blood and isolated $CD34^+$ cells, multipotent adult progenitor cells, adult stem cells and embyronic stem cells. In one embodiment, the donor cells are autologous cells, however, non-autologous cells, e.g., xenogeneic cells, may be employed. The donor cells can be expanded in vitro to provide an expanded population of donor cells for administration to a recipient animal. In addition, donor cells may be treated in vitro as exemplified below. Sources of donor cells and methods of culturing those cells are known to the art. See, for example, U.S. Pat. No. 5,130,141 and Jain et al. (*Circulation,* 103, 1920 (2001)), wherein the isolation and expansion of myoblasts from skeletal leg muscle is discussed (see also Suzuki et al., *Circulation,* 104, 1-207 (2001), Douz et al., Circulation, III-210 (2000) and Zimmerman et al., *Circulation Res.,* 90, 223 (2002)). Published U.S. Application 20020110910 discusses the isolation of and media for long term survival of cardiomyocytes. U.S. Pat. No. 5,580,779 discusses isolating myocardial cells from human atria and ventricles and inducing the proliferation of those myocardial cells. U.S. Pat. No. 5,103,821 discusses isolating and culturing SA node cells. For SA node cells, the cells may be co-cultured with stem cells or other undifferentiated cells. U.S. Pat. No. 5,543,318 discusses isolating and culturing human atrial myocytes. U.S. Pat. Nos. 6,090,622 and 6,245,566 discusses preparation of embryonic stem cells, while U.S. Pat. No. 5,486,359 discusses preparation of mesenchymal cells.

The donor cells may also be manipulated in vitro to introduce one or more desirable gene products (transgenes) to the cells. Preferably, the transgenic donor cells include a transgene that enhances cellular proliferation, cellular engraftment, cellular survival, cellular differentiation and/or cellular function, e.g., increase angiogenesis or modulate fibrosis, of the donor cells in the recipient. The expression of one or more transgenes may be employed to decrease, replace or supplement (increase) the expression of endogenous genes in the donor cells, e.g., if the donor cells are autologous cells and the donor has an inherited or acquired disease associated with aberrant expression of an endogenous gene in cardiac cells. The expression of one or more transgenes may correct the level of the gene product encoded by the transgene in the donor cells. In one embodiment the expression of the transgene is controlled by a regulatable or tissue-specific, e.g., cardiac myocyte-specific promoter. The transgene may be introduced to donor cells by any means including but not limited to liposomes, electroporation, naked DNA, or viral-mediated transduction, for instance, via adenovirus, adeno-associated virus, retrovirus or lentivirus vectors.

Donor cells may be treated in vitro by subjecting them to mechanical, electrical, or biological conditioning, or any combination thereof. The conditioning may include continuous or intermittent exposure to the exogenous stimuli. Preferred exogenous agents include those which enhance the survival, engraftment, differentiation, proliferation and/or function of donor cells after transplant.

A. Mechanical Conditioning

Mechanical conditioning includes subjecting donor cells to a mechanical stress that simulates the mechanical forces applied upon cardiac muscle cells in the myocardium due to the cyclical changes in heart volume and blood pressure. In one embodiment, a cyclic mechanical stress is applied to the donor cells. In one embodiment, the cyclical mechanical stress applied to donor cells results in the cyclical deformation of these cells, resembling the cyclical deformation (contraction) of cardiac muscle cells in vivo. The mechanical stress includes subjecting one or more donor cells, preferably a population of donor cells, to a mechanical force in one dimension and in one direction, or alternatively, in one dimension and in two or more opposite directions, for example, causing the donor cells to stretch and relax at a predetermined frequency for a predetermined duration. Mechanical conditioning can result in donor cells that are capable of contracting upon excitation by action potentials.

Mechanical conditioning preferably alters gene expression, protein synthesis, and/or the activity of one or more cellular kinases in donor cells, and in one embodiment results in proliferation and/or differentiation of the donor cells. In one embodiment, mechanical conditioning of donor cells results in an altered expression profile, e.g., an altered expression profile for genes encoding BMP, VEGF, angiotensin II, and the like, in the donor cells. In one embodiment, mechanical conditioning of donor cells results in an increase in the number and/or activity of contractile elements including actin and myosin filaments, which are protein structures that interact with each other during muscle contraction. Donor cells subjected to mechanical conditioning thus develop contractility that is characteristic of muscle cells.

In one embodiment, the mechanical conditioning includes subjecting donor cells to a mechanical force so that the donor cells are physically extended in at least one direction by approximately 5% to 20% of their length, and at a frequency of 0.25 to 2 Hz. In other words, at least one donor cell is forced to increase its length by 5% to 20% at 0.25 to 2 times per second. This simulates the mechanical tension which cardiac muscle cells are subject to under physiological conditions in vivo. In one embodiment, donor cells are plated on a controllably deformable culturing substrate in the presence of culturing media. The substrate is cyclically deformed to simulate the mechanical displacement of cardiac muscle. In one specific embodiment, the substrate includes a distensible strip made of medical grade silicone. Donor cells are plated on the distensible strip. The distensible strip is stretched and released, such that the donor cells on it change their length with the distensible strip in a manner simulating the cardiac muscle cells in vivo. One example of such an apparatus for applying mechanical stress to cells in a culture is given in Terracio et al., *In Vitro Cellular & Developmental Biology,*

24(1), 53-58, 1988, where the silicone strip is subject to calibrated mechanical tension created with a variable speed motor.

In one embodiment, the mechanical conditioning is applied continuously for a predetermined period of time. In one specific embodiment, the predetermined period is in the range of 1 to 14 days. In another embodiment, the mechanical conditioning is applied intermittently for a predetermined period of time interrupted by one or more resting (non-stimulating) periods. In one specific embodiment, the mechanical conditioning is applied with a duty cycle that is in the range of 5% to 75% for a predetermined period that is in the range of 1 to 14 days.

B. Electrical Conditioning

Electrical conditioning includes subjecting donor cells to electrical conditions that simulate the electrical conditions in the myocardium which result in contraction of the heart. In the heart, contraction results primarily from the contractions of atrial and ventricular muscle fibers. Contraction of atrial and ventricular muscle fibers is slower and is of a longer duration than the contraction of skeletal muscle. Cardiac muscle and skeletal muscle, however, share a number of common anatomic characteristics. In the same manner as skeletal muscle, cardiac muscle is made up of elongated fibers with transverse dark and light bands. The dark bands correspond to the boundaries between cells. Each fiber is made up of individual cells connected in series with each other. Cardiac muscle includes myofibrils, which are the longitudinal parallel contractile elements composed of actin and myosin filaments that are almost identical to those of the skeletal muscle. The actin and myosin filaments interdigitate and slide along each other during contraction. Contraction is caused by action potentials that propagate along or spread over the muscle fibers. The propagation of action potentials results from changes in the electrical potential across muscle cell membranes, referred to as membrane potential. The changes in the membrane potential are in turn caused by flow of sodium, potassium, and/or calcium ions across the muscle cell membranes through ion channels, which are formed by protein molecules in the cell membranes. Some types of muscle include protein structures called gap junctions through which ions flow from one muscle cell to another. Gap junctions allow the flow of ions, and hence the propagation of action potentials, directly from one cell to another. Cardiac muscle has at least two unique anatomic characteristics: a high density of calcium-sodium channels and a high density of gap junctions. These characteristics distinguish cardiac muscle from skeletal and other types of muscle.

Action potential propagates in skeletal muscle mainly via the sudden opening of fast sodium channels that allow sodium ions to enter the muscle cells. Each opening of a fast sodium channel lasts for only a few ten-thousandths of a second. In contrast, cardiac muscle includes both fast sodium channels and slow calcium-sodium channels that allow both calcium and sodium to enter the muscle cells. Each opening of a slow calcium-sodium channel lasts for several tenths of a second. This results in the long duration of contraction, which characterizes cardiac muscle.

Gap junctions in cardiac muscle fibers allow relatively free flow of ions across the cell membranes along the fiber axes. Thus, action potentials travel from one cell to another with little resistance. Cardiac muscle is a syncytium (mass of fused cells) with muscle fibers arranged in a latticework in which the fibers branch, merge, and branch again. When one cell in the syncytium becomes excited, the action potential propagates from cell to cell and spreads throughout the latticework interconnections. The heart includes two syncytiums, the atrial syncytium and the ventricular syncytium. In a normal heart, action potentials are conducted from the atrial syncytium to the ventricular syncytium through a conduction system, the A-V bundle, and the atrial syncytium contracts before the ventricular syncytium.

In one embodiment, electrical conditioning includes providing electrical stimuli such as cardiac pacing pulses to the donor cells in culture so as to cause them to contract. In another embodiment, the electrical conditioning includes providing a static electrical field to the donor cells in culture. Electrical conditioning can result in the donor cells proliferating and differentiating into cardiac muscle cells, and preferably results in cells functioning as cardiac muscle cells.

In one embodiment, electrical conditioning of donor cells results in cells with one or more characteristics of cardiac muscle cells, including a high density of calcium-sodium channels and a high density of gap junctions. Such electrical conditioning may occur in vitro and/or in vivo. Moreover, once the donor cells are implanted in the myocardium, they are subject to the pattern of contractions in the myocardium and may, if they are not cardiac muscle cells, differentiate into cardiac muscle cells. In one embodiment, the donor cells are electrically conditioned prior to implantation into the myocardium. In one embodiment, the electrical conditioning includes subjecting the donor cells to an artificially induced contraction pattern that simulates the physiological contractions of cardiac muscle cells in vivo. The contraction pattern is induced by electrical stimulation such as by cardiac pacing. In a further embodiment, the donor cells are also subjected to an electrical field stimulation that simulates the environment in the myocardium. Electrical conditioning of donor cells, including cardiac pacing and/or field stimulation, may result in an altered expression profile of the donor cells, including increased calcium-sodium channel expression and/or increased expression and/or formation of gap junctions. For instance, electrical conditioning may increase angiotensin II or VEGF expression, which in turn increases gap junction formation.

In one embodiment, pacing pulses are generated by a pacemaker or any pulse generator capable of producing the pacing pulses. The donor cells are placed in a culturing media including fluids which simulate the extracellular fluid of the myocardium. The pacing pulses are delivered to the donor cells through two electrodes placed in the culture. Parameters controlling the delivery of the cardiac pacing pulses include pacing rate, pacing voltage, and pacing pulse width, which are each selected from a physiological range to simulate the electrical activities within the myocardium. In one specific embodiment, the pacing rate is in the range of 15 to 120 beats per minute; the pacing voltage is in the range of 0.1 to 10 volts; and the pacing pulse width is in the range of 0.1 to 10 milliseconds. In one embodiment, cardiac pacing is applied to the donor cells continuously for a predetermined period of time. In one specific embodiment, the predetermined period of time is in the range of 1 to 14 days. In another embodiment, cardiac pacing is applied intermittently to the donor cells for a predetermined period that is interrupted by one or more resting (non-pacing) periods. In one specific embodiment, cardiac pacing is applied to the donor cells with a duty cycle in the range of 5% to 75% for a predetermined period that is in the range of 1 to 14 days.

In one embodiment, a static electrical field is applied to a donor cell culture. In one specific embodiment, the field strength is in the range of 1 to 100 volts per meter. In one embodiment, the electrical field is applied continuously for a predetermined period. In one specific embodiment, the predetermined period is in the range of 1 to 14 days. In another embodiment, the electrical field is applied for a predetermined period that is interrupted by one or more resting (non-stimulation) periods. In one specific embodiment, the electrical field is applied with a duty cycle of 5% to 75% for a predetermined period that is in the range of 1 to 14 days.

C. Biological Conditioning

Biological conditioning includes subjecting donor cells to exogenous agents, e.g., differentiation factors, growth factors, angiogenic proteins, survival factors, and cytokines, as well as to expression cassettes (transgenes) encoding a gene product including, but not limited to, an angiogenic protein, a growth factor, a differentiation factor, a survival factor, a cytokine, a cardiac cell-specific structural gene product, a cardiac cell-specific transcription factor, or a membrane protein, e.g., a gap junction protein, or comprising an antisense sequence, for instance, a ribozyme, or any combination thereof. The expression cassette optionally includes at least one control element such as a promoter, optionally a regulatable promoter, e.g., one which is inducible or repressible, an enhancer, or a transcription termination sequence. Preferably, the promoter and/or enhancer is one which is cell- or tissue-specific, e.g., cardiac cell-specific. For instance, the enhancer may be a muscle creatine kinase (mck) enhancer, and the promoter may be an alpha-myosin heavy chain (MyHC) or beta-MyHC promoter (see Palermo et al., *Circ. Res.*, 78, 504 (1996)).

Transgenes

In one embodiment, the transgene encodes a gene product including but not limited to an angiogenic protein, e.g., a fibroblast growth factor (FGF) such as acidic-FGF, basic-FGF, FGF-3, FGF-4, FGF-5, FGF-6, FGF-7, FGF-8 and FGF-9, vascular endothelial growth factor (VEGF), e.g., VEGF-A, VEGF-B, VEG-C, VEGF-D, VEGF-E, VEGF-F, $VEGF_{145}$, $VEGF_{121}$, $VEGF_{120}$, $VEGF_{164}$, $VEGF_{165}$, $VEGF_{189}$, and $VEGF_{206}$, IGF-1, TGF-beta, e.g., $TGF-beta_1$, leukemia inhibitory factor (LIF) alone or in combination with other cytokines, a myogenic factor, e.g., myoD, RyRZ (cardiac ryanodine receptor), Del I, myogenin, parvalbumin, Myf5, and MRF, transcription factors (GATA such as GATA-4 and dHAND/eHAND), cytokines such as cardiotrophin-1, calsequestrin, neuregulin, for instance, neuregulin 1, 2 or 3, and homeobox gene products, e.g., Csx, tinman, and the NKx family, e.g., NKx 2.5, transferrin, platelet-derived growth factor (PDGF), epidermal growth factor (EGF), adrenocorticotrophin, macrophage colony-stimulating factor, protein kinase C activators, endothelial growth factor, mutant G protein receptor kinase (GRK), adenylyl cylase (AC), e.g., cardiac AC such as human type II, V or VI adenyl cylase (U.S. Pat. No. 6,436,672), V2 vasopressin receptor, sarcoplasmic reticulum $Ca2^+$ ATPase (SERCA2a), phospholambam, N-cadherin, connexin-40, connexin-41, connexin-42, connexin-43, or connexin-45, contractable proteins, e.g., myosin heavy chain (MyHC), myosin light chain (MyLC), myosin binding protein C, actin, tropomyosin, troponin, e.g., troponin T, M protein, tropomodulin, myofibrillar protein, stress related protein, e.g., heat shock protein (HSP) such as HSP70i, HSP27, HSP40 or HSP60, α-1 antitrypsin, HF 1-a, HF-1b, MEF2, BMP-2, BMP-4, BMP-17, BMP-18, Pax7, oxytocin, oxytocin receptor, myocyte nuclear factor, Frzb (see published U.S. application 20020147329), Rb-interacting zinc finger protein (U.S. Pat. No. 6,468,985), eNOS, iNOS, serine/threonine protein phosphatase, cardiac hypertrophy factor, CT-1, α, β, γ or δ sarcoglycan, hypoxia inducible factor 1α, bcl-2, FasL, cytokine gp 130 receptor, gp130, Akt, adenosine A3 receptor, angiogenin, e.g., angiogenin-1 or angiogenin-2, TNFα, dystrophin, tafazzin, desmin, lamin, troponin C, caspase inhibitors, ERK-type of MAP kinases (p42 and p44, anti-apoptosis), IL-1B, serum releasing factor, and ILGF (I and II), NGF, growth hormone, e.g., human growth hormone, angiotensin, e.g., angiotensin II, hepatocyte growth factor (HGF), $ARK_{Ct}$, endothelial GF121, angiotensin type II receptor, p16INK4a, sodium channel protein, e.g., SCN5A, C reactive protein, MiRPI, cardiac endothelin-1, KCNEI ($I_{Ks}$), protein kinase C, HIF-1α, p38MAPK, Cox-2, phospholamban, matrix metalloproteinases, adrenergic receptors (AR) and kinases therefore, e.g., betaAR and betaARK, cytochrome oxidase B subunit III, ATP synthase subunit 6, calcium channel proteins such as voltage gated $Ca^{2+}$ channels, potassium channel proteins such as KCNA5 (Kv1.5), KCND2(Kv4.2), KCND3 (Kv 4.3, $I_{to}$), KCNEI (minK), KCNE2, KCNQ1, as well as $K^+$ inwardly rectifying channels such as Kir3.1 (KCNJ3), KCNH2 (HERG, $I_{kr}$), Kv4.3, Kir3.4, Kir6.1 and Kir6.2, the sodium-calcium exchanger ($I_{Na/Ca}$), e.g., NCKX1-4, HCN, Kir 2.1, Kir3.1/3.4, ERG, KvLQT1, Kv4.2/4.3, Kv1.4, KCh1P2, Kv1.5/3.1, $Ca_v1.2$, $Ca_v1.3$, $Ca_v3.1$, $Ca_v$ 3.3, $Na_v1.5$, platelet-derived endothelial-cell growth factor (PD-ECGF), transforming growth factor-α (TGF-α), transforming growth factor-β (TGF-β), thrombospondin (TSP), proliferin, ephrin-A1 (B61), e-selectin, chicken chemotactic and angiogenic factor (cCAF), leptin, heparin affin regulatory peptide (HARP), platelet derived growth factor (PDGF), e.g., PDGF-AA, PDGF-AB or PDGF-BB, or heparin.

In another embodiment, e.g., for cells from a mammal with an inherited or acquired disorder such as one characterized by overexpression of certain endogenous genes, the transgene may comprise antisense or ribozyme sequences which substantially correspond to the reverse complement of at least a portion of the endogenous gene, and which, when expressed in a host cell, results in a decrease in the expression of the endogenous gene. Alternatively, the transgene may comprise sequences which, after homologous recombination with the endogenous gene, result in a decrease in the expression of the endogenous gene. For instance, the use of antisense vectors resulting in the decreased expression of the following gene products may be beneficial in autologous cell therapy, gene products including, but not limited to, those which induce apoptosis, e.g., Fas, Bax1 and ApoI, or a Na/Ca exchanger, or a mitogen-activated protein (MAP) kinase, Janus kinase (JAK)/signal transducer or activator of transcription, calcium/calmodulin-dependent protein phosphatase, calcineurin, carnitine palmoyl-transferase I, matrix metalloproteinase, eNOS, iNOS, serine/threonine protein phosphatase, or stress response mitogen activated protein kinase, e.g., Junk and p38MAPK.

For purposes of the present invention, control elements, such as muscle-specific and inducible promoters, enhancers and the like, will be of particular use. Such control elements include, but are not limited to, those derived from the actin and myosin gene families, such as from the myoD gene family (Weintraub et al., *Science,* 251, 761 (1991)); the myocyte-specific enhancer binding factor MEF-2 (Cserjesi and Olson, *Mol. Cell Biol.,* 11, 4854 (1991)); control elements derived from the human skeletal actin gene (Muscat et al., *Mol. Cell Bio.,* 7, 4089 (1987)) and the cardiac actin gene; muscle creatine kinase sequence elements (Johnson et al., *Mol. Cell Biol.,* 9, 3393 (1989)) and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors (Semenza et al., *Proc. Natl. Acad. Sci. USA,* 88, 5680 (1991); Semenza et al., *J. Biol. Chem.,* 269, 23757); steroid-inducible elements and promoters, such as the glucocorticoid response element (GRE)

(Mader and White, *Proc. Natl. Acad. Sci. USA*, 90, 5603 (1993)); the fusion consensus element for RU486 induction; and elements that provide for tetracycline regulated gene expression (Dhawan et al., *Somat. Cell. Mol. Genet.*, 21, 233 (1995); Shockett et al., *Proc. Natl. Acad. Sci. USA*, 92, 6522 (1995)).

Cardiac cell restricted promoters include but are not limited to promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoter promoters may also be employed, e.g., for atrial-specific expression, the quail slow myosin chain type 3 (MyHC3) or ANP promoter, may be employed. For ventricle-specific expression, the iroquois homeobox gene may be employed. Nevertheless, other promoters and/or enhancers which are not specific for cardiac cells or muscle cells, e.g., RSV promoter, may be employed in the expression cassettes and methods of the invention.

Other sources for promoters and/or enhancers are promoters and enhancers from the Csx/NKX 2.5 gene, titin gene, α-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

Preferably, the transgenic donor cells include a transgene that enhances the proliferation, engraftment, survival, differentiation and/or function of the donor cells and/or decreases, replaces or supplements (increases) the expression of endogenous genes in the donor cells. In one embodiment, the expression of the transgene is controlled by a regulatable or tissue-specific, e.g., cardiomyocyte-specific promoter. Optionally, a combination of vectors each with a different transgene can be employed.

Delivery of exogenous transgenes may be accomplished by any means, e.g., transfection with naked DNA, e.g., a vector comprising the transgene, liposomes, calcium-mediated transformation, electroporation, or transduction, e.g., using recombinant viruses. A number of transfection techniques are generally known in the art. See, e.g., Graham et al., *Virology*, 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi, *Cell*, 22, 479 (1980)), electroporation (Shigekawa et al., *BioTechniques*, 6, 742 (1988)), liposome-mediated gene transfer (Mannino et al., *BioTechniques*, 6, 682 (1988)), lipid-mediated transduction (Felgner et al., *Proc. Natl. Acad. Sci. USA*, 84, 7413 (1987)), and nucleic acid delivery using high-velocity microprojectiles (Klein et al., *Nature*, 327, 70 (1987)). Preferred recombinant viruses to deliver exogenous transgenes to cells include recombinant lentiviruses, retroviruses, adenoviruses, adeno-associated viruses (AAV), and herpes viruses including cytomegalovirus.

In one embodiment, recombinant AAV (rAAV) is employed to deliver a transgene to donor cells. Myoblasts are transduced either while actively dividing, or as a differentiated cell culture. Differentiation is induced by placing sub-confluent myoblasts in DMEM containing 2% horse serum and standard concentrations of glutamine and penicillin-streptomycin for an interval of four days prior to transduction. Verification of differentiation is by microscopic analysis to determine the presence of multinucleated myotubes in culture. Myotubes (differentiated cells) or myoblasts (dividing cells) are transduced in culture.

Other Exogenous Agents

In another embodiment, the exogenous agent includes but is not limited to an angiogenic protein, e.g., a FGF such as acidic-FGF, basic-FGF, and FGF-5, VEGF, e.g., $VEGF_{145}$, $VEGF_{121}$, $VEGF_{120}$, $VEGF_{164}$, $VEGF_{165}$, $VEGF_{189}$, and $VEGF_{206}$, IGF-1, TGF-beta, e.g., TGF-beta$_1$, LIF alone or in combination with other cytokines, a myogenic factor, e.g., myoD, RyRZ (cardiac ryanodine receptor), Del I, myogenin, parvalbumin, Myf5, and MRF, GATA such as GATA-4 and dHAND/eHAND, cytokines such as cardiotrophin-1, calsequestrin, neuregulin, for instance, neuregulin 1, 2 or 3, and homeobox gene products, e.g., Csx, tinman, and the NKx family, e.g., NKx 2.5, transferrin, PDGF, EGF, adrenocorticotrophin, macrophage colony-stimulating factor, protein kinase C activators, endothelial growth factor, β2 adrenergic receptor (1 or 2), mutant G protein receptor kinase (GRK), AC, e.g., cardiac AC such as human type II, V or VI adenyl cylase (U.S. Pat. No. 6,436,672), V2 vasopressin receptor, SERCA2a, phospholambam, β-adrenergic receptor kinase, N-cadherin, connexin-40, connexin-42, connexin-43, MyHC, MyLC, myosin binding protein C, actin, tropomyosin, troponin, e.g., troponin T, M protein, tropomodulin, myofibrillar protein, stress related protein, e.g., HSP such as HSP70i, HSP27, HSP40 or HSP60, α-1 antitrypsin, HF1-a, HF-1b, MEF2, HGF, BMP-2, BMP4, BMP-17, BMP-18, Pax7, oxytocin, oxytocin receptor, myocyte nuclear factor, Frzb (see published U.S. application 20020147329), Rb-interacting zinc finger protein (U.S. Pat. No. 6,468,985), eNOS, iNOS, serine/threonine protein phosphatase, cardiac hypertrophy factor, CT-1, α, β, γ or 6 sarcoglycan, hypoxia inducible factor 1α, bcl-2, FasL, cytokine gp 130 receptor, gp130, Akt, adenosine A3 receptor, angiogenin, e.g., angiogenin-1 or angiogenin-2, TNFα, dystrophin, tafazzin, desmin, lamin, troponin C, caspase inhibitors, ERK-type of MAP kinases (p42 and p44, anti-apoptosis), IL-1B, serum releasing factor, and ILGF (I and II), NGF, growth hormone, e.g., human growth hormone, angiotensin, e.g., angiotensin II, inotropes, norepinephrine, retinoic acid, preconditioned media, e.g., from ES cells which contains a plurality of growth factors, or other biological agents disclosed herei, or dexamethasone or 5 azacytidine. Such agents may also be administered to a mammal prior to, during, or after cell therapy, or any combination thereof.

Compositions, Dosages and Routes of Administration

The amount of agent administered, including agents released from a device of the invention or agents including cells and/or gene therapy vectors which are exogenously administered in conjunction with electrical and agent therapies described herein, will vary depending on various factors including, but not limited to, the agent chosen, the disease, whether prevention or treatment is to be achieved, and if the agent is modified for bioavailability and in vivo stability. Thus, the agents of the invention may be employed in conjunction with other therapies, e.g., therapies for ischemia or arrhythmias, including gene therapies and/or cell therapies, e.g., see U.S. patent application Ser. No. 10/723,258, filed on Nov. 25, 2003, entitled "METHOD AND APPARATUS FOR CELL AND ELECTRICAL THERAPY OF LIVING CELLS" and U.S. patent application Ser. No. 10/788,906, filed on Feb. 27, 2004, entitled "METHOD AND APPRATUS FOR DEVICE CONTROLLED GENE EXPRESSION", the disclosures of which are incorporated herein by reference in their entirety.

Administration of the agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes, although local administration of at least one agent via an implantable device is a preferred embodiment of the invention. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

Pharmaceutical formulations containing the agents of the invention can be prepared by procedures known in the art using well known and readily available ingredients. For example, the agent can be formulated with common excipients, diluents, or carriers. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols. The formulations can include buffering agents such as calcium carbonate, magnesium oxide and magnesium carbonate, as well as, inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and gelatin, microcrystalline cellulose, sodium lauryl sulfate, starch, talc, or titanium dioxide, or liquid vehicles such as polyethylene glycols (PEGs) and vegetable oil.

The pharmaceutical formulations of the agents of the invention can also take the form of an aqueous or anhydrous solution or dispersion, or alternatively the form of an emulsion or suspension.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

Additionally, the agents are well suited to formulation as sustained release dosage forms and the like. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, epicardial patch, leads, and the like.

The formulations and compositions described herein may also contain other ingredients such as antimicrobial agents, or preservatives. Furthermore, as described herein the active ingredients may also be used in combination with other therapeutic agents, or therapies, for instance, cell therapy.

The cells to be administered may be a population of individual cells or cells grown in culture so as to form a two dimensional or three dimensional structure. The number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered to, e.g., injected, the region of interest, for instance, infarcted and tissue surrounding infarcted tissue. Agents which may enhance cardiac function or stimulate angiogenesis include but are not limited to pyruvate, catecholamine stimulating agents, fibroblast growth factor, e.g., basic fibroblast growth factor, acidic fibroblast growth factor, fibroblast growth factor-4 and fibroblast growth factor-5, epidermal growth factor, platelet-derived growth factor, vascular endothelial growth factor (e.g., $VEGF_{121}$, $VEGF_{145}$, $VEGF_{165}$, $VEGF_{189}$ or $VEGF_{206}$), tissue growth factors and the like. Such agents may optionally be present in a composition comprising the donor cells or administered separately.

The cells are administered during a prophylactic, diagnostic or therapeutic vascular procedure or an invasive or minimally invasive surgical procedure. In one embodiment, the cells are administered post-MI, within hours, e.g., 1 to 12 hours, to days, e.g., 1 to 2 days, and up to one or more weeks after MI. Preferably, the administration of donor cells is prior to scar formation. The cells may be administered intravenously, transvenously, intramyocardially or by any other convenient route, and delivered by a needle, catheter, e.g., a catheter which includes an injection needle or infusion port, or other suitable device.

In General

All publications, patents and patent applications referred to are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A system adapted to be coupled to a heart having myocardial tissue and a myocardial infarct (MI) region, the system comprising:

an implantable agent delivery device containing one or more agents that promote myocardial tissue replacement and adapted to deliver the one or more agents to the MI region, wherein the one or more agents that promote myocardial tissue replacement enhance migration, implantation, or proliferation of stem cells in the MI region and reduce scar formation; and an implantable ventricular-assist device (VAD) including:
   a sensor to sense one or more signals indicative of one or more of a strain of the myocardial tissue and a size of the MI region;
   a pump to assist the heart in blood pumping;
   a VAD controller coupled to the pump, the VAD controller adapted to control the operation of the pump using the sensed one or more signals for enhancing one or more effects of the one or more agents; and
an agent delivery controller coupled to the implantable agent delivery device, the agent delivery controller adapted to control the delivery of the one or more agents using the sensed one or more signals in temporal coordination with the operation of the pump.

2. The system of claim 1, wherein the one or more agents comprise one or more agents that change one or more mechanical properties of tissue in the MI region.

3. The system of claim 1, wherein the one or more agents comprise one or more agents that promote vascularization in the MI region.

4. The system of claim 1, wherein the one or more agents comprise one or more agents that reduce adverse remodeling of tissue in the MI region.

5. The system of claim 1, wherein the one or more agents comprise one or more agents that modulate hypertrophic signaling in the MI region.

6. The system of claim 1, wherein the one or more agents comprise one or more agents that modulate fibrosis signaling in the MI region.

7. The system of claim 1, wherein the one or more agents comprise one or more of stem cell growth factor (SCF), granulocyte colony-stimulation factor (G-CSF), granulocyte macrophage colony-stimulating growth factor (GM-CSF), stem cell homing factor (SDF-1), bone morphogenetic protein 2 (BMP-2), Wnt protein, a gene encoding SCF, a gene encoding G-CSF, a gene encoding GM-CSF, a gene encoding SDF-1, a gene encoding BMP-2, and a gene encoding Wnt protein.

8. The system of claim 1, wherein the one or more agents comprise one or more agents that enhance myocardial tissue regeneration.

9. The system of claim 1, wherein the one or more agents comprise a cytokine.

10. The system of claim 1, the one or more agents comprise one or more of hepatocyte growth factor (HGF), insulin-like growth factor (IGF), fibroblast growth factor (FGF), transforming growth factor-beta (TGF-$\beta$), a gene encoding HGF, a gene encoding IGF, a gene encoding FGF, and a gene encoding TGF-$\beta$.

11. The system of claim 1, further comprising an agent eluting lead coupled to the agent delivery device.

12. The system of claim 11, further comprising an implantable device including the agent delivery device and the VAD.

13. The system of claim 1, wherein the agent delivery device comprises an agent eluting stent configured for placement in or near the MI region.

14. The system of claim 1, wherein the agent delivery device comprises an agent eluting epicardial patch configured for placement in or near the MI region.

15. The system of claim 1, wherein the sensor comprises an ischemia sensor to sense a signal indicative of an ischemic condition.

16. The system of claim 1, wherein the sensor comprises a cardiac sensing circuit to sense at least one electrogram indicative of arrhythmia.

17. The system of claim 1, wherein the sensor comprises a displacement sensor to sense a signal indicative of the strain of myocardial tissue.

18. The system of claim 1, wherein the sensor comprises a remodeling sensor to sense a signal indicative of the size of the MI region.

19. The system of claim 1, wherein the sensor comprises a sensor to sense hypertrophic signaling.

20. The system of claim 19, wherein the sensor comprises a sensor to sense the concentration of endothelin-1, brain natriuretic peptide (BNP) or p38MAPK.

21. The system of claim 1, wherein the sensor comprises a metabolic sensor to sense a signal indicative of a metabolic need of a body.

22. The system of claim 1, wherein the sensor comprises a temperature sensor to sense a signal indicative of a perfusion of thermal energy through myocardial tissue.

23. The system of claim 1, wherein the sensor comprises a metabolic sensor to sense one or more signals indicative of a cardiac metabolism level.

24. The system of claim 23, wherein the metabolic sensor includes at least one of a pH sensor, an oxygen pressure ($PO_2$) sensor, a carbon dioxide pressure ($PCO_2$) sensor, a glucose sensor, a creatine sensor, a C-creative protein sensor, a creatine kinase sensor, and a creatine kinase-MB sensor.

25. The system of claim 1, wherein the agent delivery device comprises an electrically controlled polymer containing the one or more agents, the polymer adapted to release the one or more agents at a rate controlled by an amplitude of the agent delivery control signal.

26. The system of claim 1, wherein the agent delivery controller comprises a command receiver to receive an external command, and wherein the agent delivery controller is adapted to produce the agent delivery control signal in response to the external command.

27. The system of claim 26, wherein the VAD is an implantable VAD, and the agent delivery device is an implantable agent delivery device, and further comprising an external system communicatively couple to the implantable VAD, the external system including a command transmitter to transmit the external command to the implantable VAD.

28. The system of claim 27, wherein the external system comprises a user input to receive a user command, and wherein the command transmitter transmits the external command in response to the user command.

29. The system of claim 28, wherein the external system comprises:
   an external device communicatively coupled to the implantable VAD;
   a network coupled to the external device; and
   a remote device coupled to the network to provide for communication with the implantable VAD from a remote location.

* * * * *

UNITED STATES PATENT AND TRADEMARK OFFICE
CERTIFICATE OF CORRECTION

| | | |
|---|---|---|
| PATENT NO. | : 7,828,711 B2 | Page 1 of 1 |
| APPLICATION NO. | : 10/919016 | |
| DATED | : November 9, 2010 | |
| INVENTOR(S) | : Jeffrey Ross et al. | |

It is certified that error appears in the above-identified patent and that said Letters Patent is hereby corrected as shown below:

In column 31, line 48, in Claim 10, after "claim 1," insert -- wherein --.

Signed and Sealed this
Fifteenth Day of February, 2011

David J. Kappos
*Director of the United States Patent and Trademark Office*